United States Patent
Halasa et al.

(10) Patent No.: US 6,753,447 B2
(45) Date of Patent: Jun. 22, 2004

(54) FUNCTIONALIZED MONOMERS FOR SYNTHESIS OF RUBBERY POLYMERS

(75) Inventors: Adel Farhan Halasa, Bath, OH (US); Wen-Liang Hsu, Cuyahoga Falls, OH (US); Naoya Ogata, Tokyo (JP)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 10/370,969

(22) Filed: Feb. 20, 2003

(65) Prior Publication Data

US 2004/0044202 A1 Mar. 4, 2004

Related U.S. Application Data

(60) Provisional application No. 60/434,892, filed on Dec. 19, 2002, and provisional application No. 60/404,081, filed on Aug. 16, 2002.

(51) Int. Cl.[7] .............................................. C07C 209/08
(52) U.S. Cl. ...................... 564/482; 548/579; 548/950; 546/352; 540/450; 540/612
(58) Field of Search .......................... 564/482; 548/579, 548/950; 546/352; 540/450, 612

(56) References Cited

PUBLICATIONS

Polymer Preprints (2000), 41(1), p. 97–98.*
Database CAPLUS on STN, Acc. No. 2000:208056, Wu et al., Polymer Preprints (2000), 41(1), p. 97–98 (abstract).*
Database CAPLUS on STN, Acc. No. 1988:5302, Kurginyan et al, Armyanskii Khimicheskii Zhurnal (1986), 39(8), p. 516–26 (abstract).*

* cited by examiner

Primary Examiner—Brian J. Davis
(74) Attorney, Agent, or Firm—Alvin T. Rockhill

(57) ABSTRACT

This invention discloses a process for synthesizing an amine functionalized monomer that comprises (1) reacting a secondary amine with a 2,3-dihalopropene to produce a vinyl halide containing secondary amine having a structural formula selected from the group consisting of

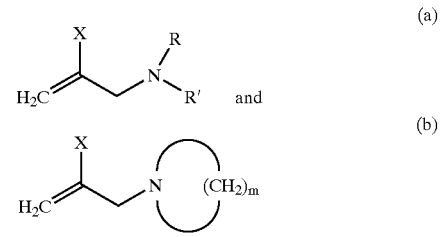

wherein R and R' can be the same or different and represent allyl, alkoxyl or alkyl groups containing from 1 to about 10 carbon atoms, and wherein X represents a halogen atom, and wherein m represents an integer from 4 to about 10, and wherein X represents a halogen atom; and (2) reacting the vinyl halide containing secondary amine with a vinyl magnesium halide to produce the monomer having a structural formula

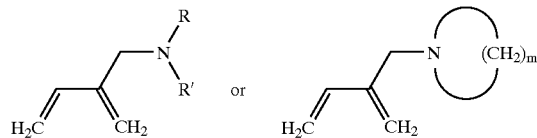

wherein R and R' can be the same or different and represent alkyl, allyl or alkoxyl groups containing from 1 to about 10 carbon atoms, and wherein m represents an integer from about 4 to about 10.

17 Claims, No Drawings

FUNCTIONALIZED MONOMERS FOR SYNTHESIS OF RUBBERY POLYMERS

This application claims the benefit of U.S. Provisional Application Serial No. 60/404,081, filed on Aug. 16, 2002, and U.S. Provisional Application Serial No. 60/434,892, filed on Dec. 19, 2002.

BACKGROUND OF THE INVENTION

It is important for rubbery polymers that are used in tires, hoses, power transmission belts and other industrial products to have good compatibility with fillers, such as carbon black and silica. To attain improved interaction with fillers such rubbery polymers can be functionalized with various compounds, such as amines. U.S. Pat. No. 4,935,471 discloses a process for preparing a polydiene having a high level of affinity for carbon black which comprises reacting a metal terminated polydiene with a capping agent selected from the group consisting of (a) halogenated nitrites having the structural formula X—A—C≡N, wherein X represents a halogen atom and wherein A represents an alkylene group containing from 1 to 20 carbon atoms, (b) heterocyclic aromatic nitrogen containing compounds, and (c) alkyl benzoates. The capping agents disclosed by U.S. Pat. No. 4,935,471 react with metal terminated polydienes and replace the metal with a terminal cyanide group, a heterocyclic aromatic nitrogen containing group or a terminal group which is derived from an alkyl benzoate. For example, if the metal terminated polydiene is capped with a nitrile, it will result in the polydiene chains being terminated with cyanide groups. The use of heterocyclic aromatic nitrogen containing compounds as capping agents can result in the polydiene chains being terminated with a pyrrolyl group, an imidazolyl group, a pyrazolyl group, a pyridyl group, a pyrazinyl group, a pyrimidinyl group, a pyridazinyl group, an indolizinyl group, an isoindolyl group, a 3-H-indolyl group, a cinnolinyl group, a pyridinyl group, a .beta.-carbolinyl group, a perimidinyl group, a phenanthrolinyl group or the like.

U.S. Pat. No. 4,935,471 also discloses that lithium amides are highly preferred initiators because they can be used to prepare polydienes which are terminated with polar groups at both ends of their polymer chains. The extra polar functionality provided by lithium amides results in increased interaction with carbon black resulting in better polymer-carbon black dispersion. The lithium amides disclosed by U.S. Pat. No. 4,935,471 include lithium pyrrolidide. U.S. Pat. No. 4,935,471 also indicates that preferred initiators include amino alkyl lithium compounds of the structural formula:

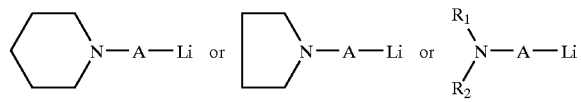

wherein A represents an alkylene group containing from 1 to 20 carbon atoms, and wherein $R_1$ and $R_2$ can be the same or different and represent alkyl groups containing from 1 to 20 carbon atoms.

It is also desirable for synthetic rubbers to exhibit low levels of hysteresis. This is particularly important in the case of rubbers that are used in tire tread compounds. Such polymers are normally compounded with sulfur, carbon black, accelerators, antidegradants and other desired rubber chemicals and are then subsequently vulcanized or cured into the form of a useful article. It has been established that the physical properties of such cured rubbers depend upon the degree to which the carbon black is homogeneously dispersed throughout the polydiene rubber. This is in turn related to the level of affinity that carbon black has for the rubber. This can be of practical importance in improving the physical characteristics of rubber articles that are made utilizing polydiene rubbers. For example, the rolling resistance and tread wear characteristics of tires can be improved by increasing the affinity of carbon black to the rubbery polymers utilized therein. Therefore, it would be highly desirable to improve the affinity of a given polydiene rubber for carbon black and/or silica. This is because a better dispersion of carbon black throughout polydiene rubbers which are utilized in compounding tire tread compositions results in a lower hysteresis value and consequently tires made therefrom have lower rolling resistance. It is also known that a major source of hysteresis is due to polymer chain ends that are not capable of full elastic recovery. Accordingly, improving the affinity of the rubber chain ends to the filler is extremely important in reducing hysteresis.

U.S. Pat. No. 6,080,835 discloses a functionalized elastomer comprising: a functional group defined by the formula:

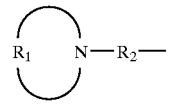

where $R_1$ is a selected from the group consisting of a divalent alkylene group, an oxy-alkylene group, an amino alkylene group, and a substituted alkylene group, each group having from about 6 to about 20 carbon atoms, $R_2$ is covalently bonded to the elastomer and is selected from the group consisting of a linear-alkylene group, a branched-alkylene group, and a cyclo-alkylene group, each group having from about 2 to about 20 carbon atoms.

U.S. Pat. No. 5,932,662 discloses a method of preparing a polymer comprising: preparing a solution of one or more anionically polymerizable monomers in a solvent; and, polymerizing under effective conditions, said monomers in the presence of a polymerization initiator having the formula

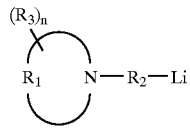

wherein $R_1$ is a divalent alkylene, an oxy- or amino-alkylene having from 6 to about 20 carbon atoms; and, $R_2$ is a linear alkylene, branched-alkylene, or cyclo-alkylene having from about 2 to about 20 carbon atoms, Li is a lithium atom bonded directly to a carbon atom of $R_2$; and $R_3$ is a tertiary amino, an alkyl having from about 1 to about 12 carbon atoms; an aryl having from about 6 to about 20 carbon atoms; an alkaryl having from about 7 to about 20 carbon atoms; an alkenyl having from about 2 to about 12 carbon atoms; a cycloalkyl having from about 5 to about 20 carbon atoms; a cycloalkenyl having from about 5 to about 20 carbon atoms; a bicycloalkyl having from about 6 to about 20 carbon atoms; and, a bicycloalkenyl having from about 6 to about 20 carbon atoms; where n is an integer of from 0 to about 10.

U.S. Pat. No. 6,084,025 discloses a functionalized polymer prepared by a process comprising the steps of: preparing a solution of a cyclic amine compound, an organolithium compound, and from 3 to about 300 equivalents, based upon one equivalent of lithium, of a monomer selected from vinyl aromatic monomers, and mixtures thereof, where said cyclic amine compound is defined by the formula

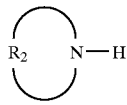

where $R_2$ is selected from the group consisting of an alkylene, substituted alkylene, bicycloalkane, and oxy- or N-alkylamino-alkylene group having from about 3 to about 16 methylene groups, N is a nitrogen atom, and H is a hydrogen atom, thereby forming a polymerization initiator having the formula $A(SOL)_y Li$, where Li is a lithium atom, SOL is a divalent hydrocarbon group having from 3 to about 300 polymerized monomeric units, y is from 0.5 to about 3, and A is a cyclic amine radical derived from said cyclic amine; charging the solution containing $A(SOL)_y Li$ with from about 0.01 to about 2 equivalents per equivalent of lithium of a chelating reagent, and an organic alkali metal compound selected from compounds having the formula $R_4 OM$, $R_5 C(O)OM$, $R_6 R_7 NM$, and $R_8 SO_3 M$, where $R_4$, $R_5$, $R_6$, $R_7$, and $R_8$ are each selected from alkyls, cycloalkyls, alkenyls, aryls, or phenyls, having from 1 to about 12 carbon atoms; and where M is Na, K, Rb or Cs, and sufficient monomer to form a living polymeric structure; and quenching the living polymeric structure.

In the initiator systems of U.S. Pat. No. 6,084,025 a chelating reagent can be employed to help prevent heterogeneous polymerization. The reagents that are reported as being useful include tetramethylethylenediamine (TMEDA), oxolanyl cyclic acetals, and cyclic oligomeric oxolanyl alkanes. The oligomeric oxolanyl alkanes may be represented by the structural formula:

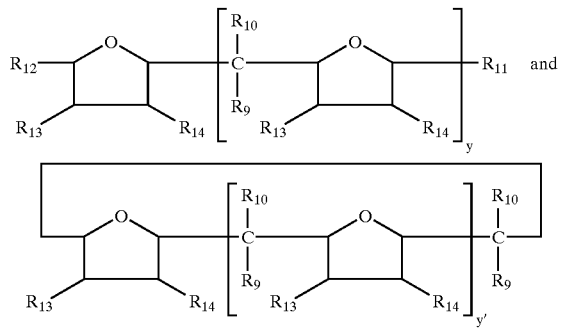

wherein $R_9$ and $R_{10}$ independently are hydrogen or an alkyl group and the total number of carbon atoms in $—CR_9 R_{10}—$ ranges between one and nine inclusive; y is an integer of 1 to 5 inclusive; y' is an integer of 3 to 5 inclusive; and $R_{11}$, $R_{12}$, $R_{13}$, and $R_{14}$ independently are $—H$ or $—C_n H_{2n+1}$, wherein n=1 to 6.

U.S. Pat. No. 6,344,538 discloses functionalized monomers and polymerized functionalized monomers selected from the group consisting of 2-(N,N-dimethylaminomethyl)-1,3-butadiene, 2-(N,N-diethylaminomethyl)-1,3-butadiene, 2-(N,N-di-n-propylaminomethyl)-1,3-butadiene, 2-(cyanomethyl)-1,3-butadiene, 2-(aminomethyl)-1,3-butadiene, 2-(hydroxymethyl)-1,3-butadiene, 2-(carboxymethy)-1,3-butadiene, 2-(acetoxymethyl)-1,3-butadiene, 2-(2-alkoxy-2-oxoethyl)-1,3-butadiene, 2,3-bis(cyanomethyl)-1,3-butadiene, 2,3-bis(dialkylaminomethyl)-1,3-butadiene, 2,3-bis(4-ethoxy-4-4-oxobutyl)-1,3-butadiene and 2,3-bis(3-cyanopropyl)-1,3-butadiene, and methods for preparing such functionalized diene monomers and polymers.

SUMMARY OF THE INVENTION

The present invention relates to functionalized monomers that can be polymerized into rubbery polymers having low hysteresis and good compatibility with fillers, such as carbon black and silica. The functionalized monomers of this invention are typically incorporated into the rubbery polymer by being copolymerized with one or more conjugated diolefin monomers and optionally other monomers that are copolymerizable therewith, such as vinyl aromatic monomers. In any case, improved polymer properties are realized because the functionalized monomers of this invention improve the compatibility of the rubber with the types of fillers that are typically used in rubber compounds, such as carbon black and silica.

This invention more specifically discloses monomers that are particularly useful for copolymerization with conjugated diolefin monomers to produce rubbery polymers having better compatibility with fillers. The monomers of this invention have a structural formula selected from the group consisting of

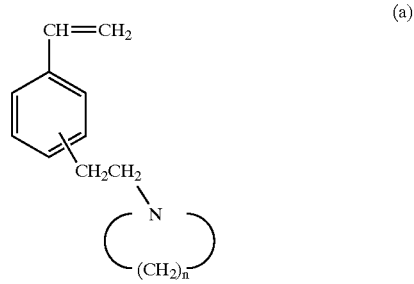

(a)

wherein n represents an integer from 4 to about 10,

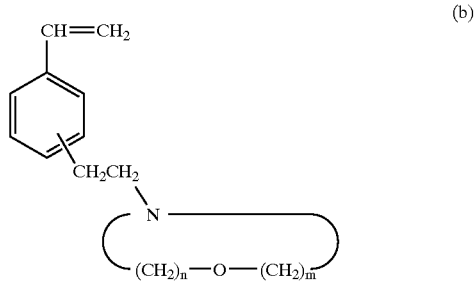

(b)

wherein n represents an integer from 0 to about 10 and wherein m represents an integer from 0 to about 10, with the proviso that the sum of n and m is at least 4;

(c)

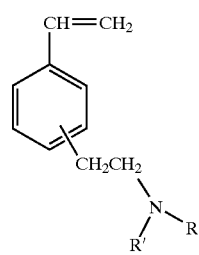

wherein R and R' can be the same or different and represent alkyl, allyl groups or alkoxy groups containing from about 1 to about 10 carbon atoms;

(d)

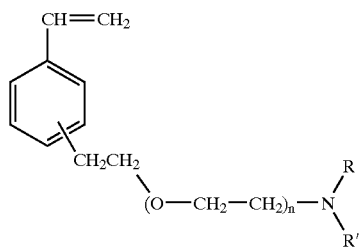

wherein n represents an integer from 1 to about 10, and wherein R and R' can be the same or different and represent alkyl groups containing from about 1 to about 10 carbon atoms;

(e)

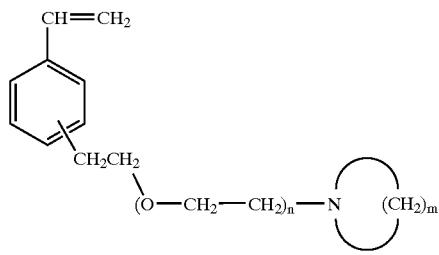

wherein n represents an integer from 1 to about 10 and wherein m represents an integer from 4 to about 10;

(f)

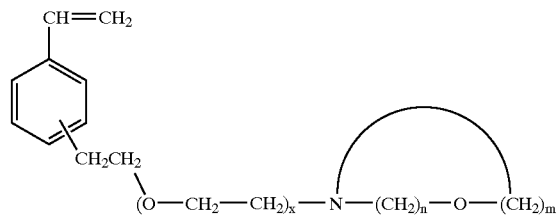

wherein x represents an integer from about 1 to about 10, wherein n represents an integer from 0 to about 10 and wherein m represents an integer from 0 to about 10, with the proviso that the sum of n and m is at least 4;

(g)

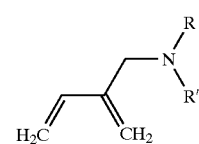

wherein R and R' can be the same or different and represent allyl, alkoxyl or alkyl groups containing from 1 to about 10 carbon atoms, (h)

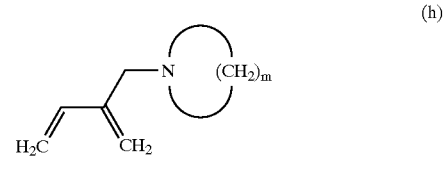

wherein m represents an integer from about 4 to about 10;

(i)

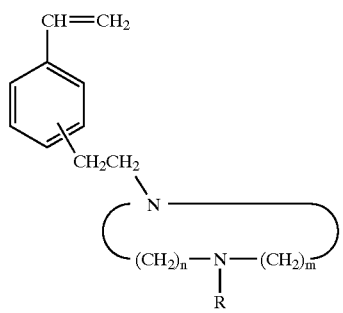

wherein R represents a hydrogen atom or an alkyl group containing from 1 to about 10 carbon atoms, wherein n represents an integer from 0 to about 10, and wherein m represents an integer from 0 to about 10, with the proviso that the sum of n and m is at least 4; and (j)

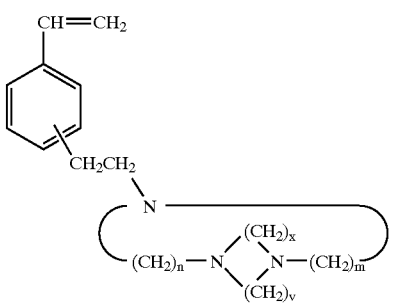

wherein n represents an integer from 0 to about 10, wherein m represents an integer from 0 to about 10, wherein x represents an integer from 1 to about 10, and wherein y represents an integer from 1 to about 10.

The present invention further discloses a process for synthesizing an amine functionalized monomer that comprises (1) reacting a secondary amine with a 2,3-dihalopropene to produce a vinyl halide containing secondary amine having a structural formula selected from the group consisting of (a)

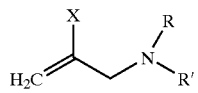

wherein R and R' can be the same or different and represent allyl, alkoxyl or alkyl groups containing from 1 to about 10 carbon atoms, and wherein X represents a halogen atom, and (b)

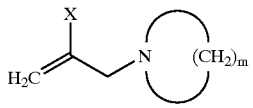

wherein m represents an integer from 4 to about 10, and wherein X represents a halogen atom; and (2) reacting the vinyl halide containing secondary amine with a vinyl magnesium halide to produce the monomer, wherein the monomer has a structural formula selected from the group consisting of (a)

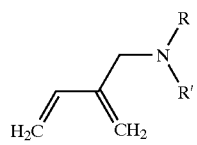

wherein R and R' can be the same or different and represent allyl, alkoxyl or alkyl groups containing from 1 to about 10 carbon atoms, and (b)

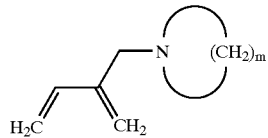

wherein m represents an integer from about 4 to about 10.

The present invention also reveals a rubbery polymer which is comprised of repeat units that are derived from (1) at least one conjugated diolefin monomer, and (2) at least one monomer having a structural formula selected from the group consisting of (a)

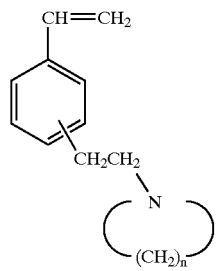

wherein n represents an integer from 4 to about 10, (b)

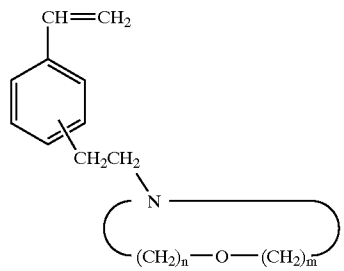

wherein n represents an integer from 0 to about 10 and wherein m represents an integer from 0 to about 10, with the proviso that the sum of n and m is at least 4;

(c)

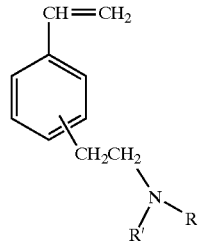

wherein R and R' can be the same or different and represent alkyl, allyl groups or alkoxy groups containing from about 1 to about 10 carbon atoms;

(d)

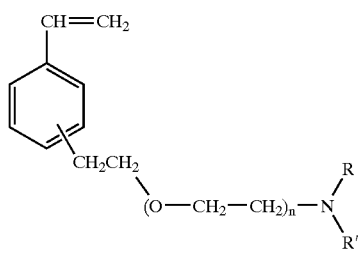

wherein n represents an integer from 1 to about 10, and wherein R and R' can be the same or different and represent alkyl groups containing from about 1 to about 10 carbon atoms;

(e)

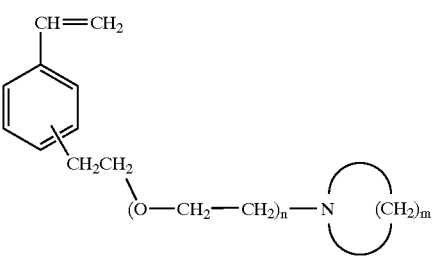

wherein n represents an integer from 1 to about 10 and wherein m represents an integer from 4 to about 10;

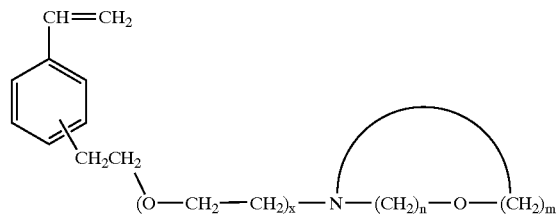
(f)

wherein x represents an integer from about 1 to about 10, wherein n represents an integer from 0 to about 10 and wherein m represents an integer from 0 to about 10, with the proviso that the sum of n and m is at least 4;

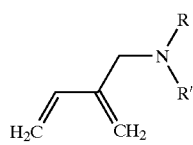
(g)

wherein R and R' can be the same or different and represent allyl, alkoxyl or alkyl groups containing from 1 to about 10 carbon atoms,

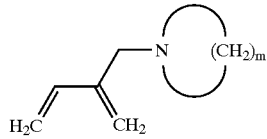
(h)

wherein m represents an integer from about 4 to about 10;

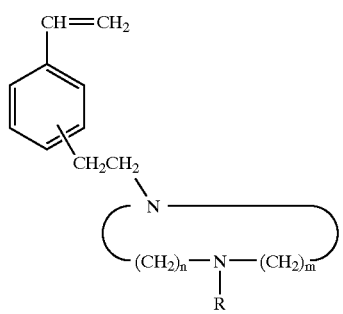
(i)

wherein R represents a hydrogen atom or an alkyl group containing from 1 to about 10 carbon atoms, wherein n represents an integer from 0 to about 10, and wherein m represents an integer from 0 to about 10, with the provision that the sum of n and m is at least 4; and

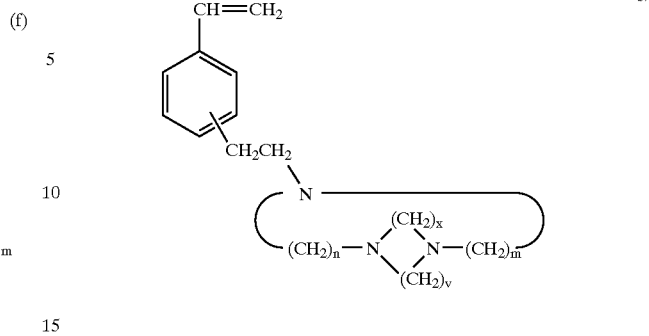
(j)

wherein n represents an integer from 0 to about 10, wherein m represents an integer from 0 to about 10, wherein x represents an integer from 1 to about 10, and wherein y represents an integer from 1 to about 10.

The subject invention further discloses a process for synthesizing a rubbery polymer that comprises copolymerizing at least one conjugated diolefin monomer and at least one functionalized monomer in an organic solvent at a temperature which is within the range of 20° C. to about 100° C., wherein the polymerization is initiated with an anionic initiator or a Zeigler-Natta catalyst system, and wherein the functionalized monomer has a structural formula selected from the group consisting of

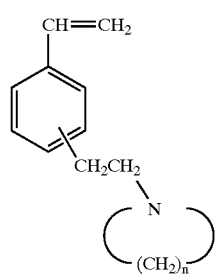
(a)

wherein n represents an integer from 4 to about 10,

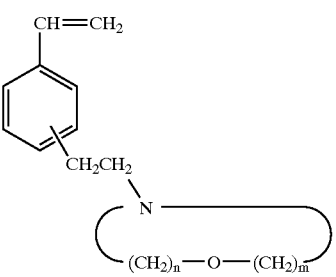
(b)

wherein n represents an integer from 0 to about 10 and wherein m represents an integer from 0 to about 10, with the proviso that the sum of n and m is at least 4;

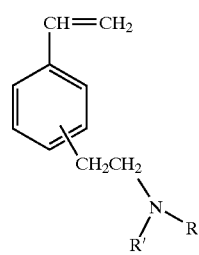
(c)

wherein R and R' can be the same or different and represent alkyl, allyl groups or alkoxy groups containing from about 1 to about 10 carbon atoms;

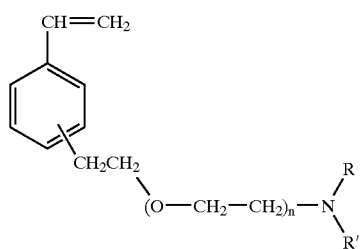
(d)

wherein n represents an integer from 1 to about 10, and wherein R and R' can be the same or different and represent alkyl groups containing from about 1 to about 10 carbon atoms;

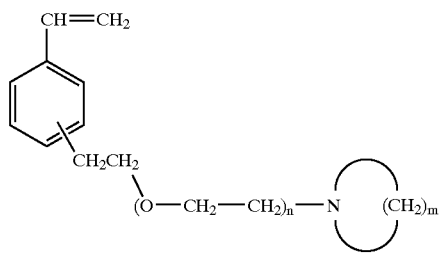
(e)

wherein n represents an integer from 1 to about 10 and wherein m represents an integer from 4 to about 10;

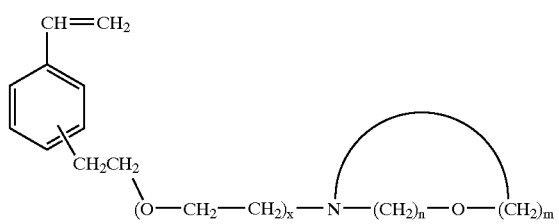
(f)

wherein x represents an integer from about 1 to about 10, wherein n represents an integer from 0 to about 10 and wherein m represents an integer from 0 to about 10, with the proviso that the sum of n and m is at least 4;

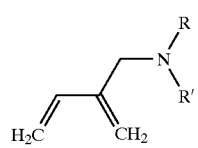
(g)

wherein R and R' can be the same or different and represent alkyl groups containing from 1 to about 10 carbon atoms,

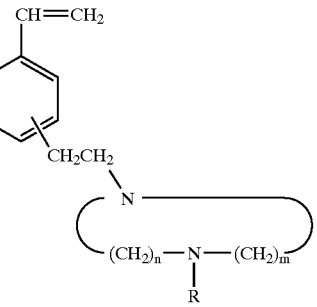
(h)

wherein m represents an integer from about 4 to about 10;

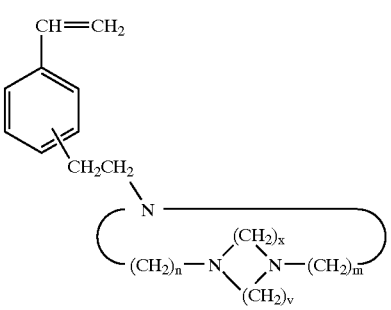
(i)

wherein R represents a hydrogen atom or an alkyl group containing from 1 to about 10 carbon atoms, wherein n represents an integer from 0 to about 10, and wherein m represents an integer from 0 to about 10, with the proviso that the sum of n and m is at least 4; and and (j)

wherein n represents an integer from 0 to about 10, wherein m represents an integer from 0 to about 10, wherein x represents an integer from 1 to about 10, and wherein y represents an integer from 1 to about 10.

The present invention also discloses a process synthesizing functionalized styrene monomer that comprises (1) reacting a secondary amine with sodium hydroxide to produce a sodium amide, and (2) reacting the sodium amide with a vinyl benzyl halide to produce the functionalized styrene monomer.

The subject invention further reveals a tire which is comprised of a generally toroidal-shaped carcass with an outer circumferential tread, two spaced beads, at least one ply extending from bead to bead and sidewalls extending radially from and connecting said tread to said beads, wherein said tread is adapted to be ground-contacting, and wherein said tread is comprised of (I) a filler, and (II) rubbery polymer which is comprised of repeat units that are derived from (1) at least one conjugated diolefin monomer, and (2) at least one monomer having a structural formula selected from the group consisting of

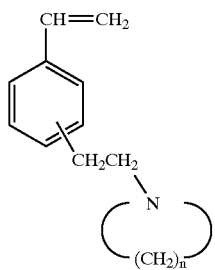

(a)

wherein n represents an integer from 4 to about 10,

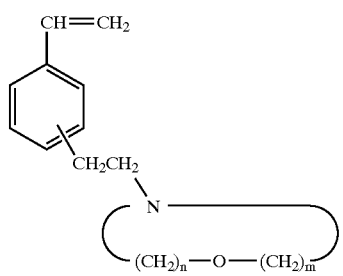

(b)

wherein n represents an integer from 0 to about 10 and wherein m represents an integer from 0 to about 10, with the proviso that the sum of n and m is at least 4;

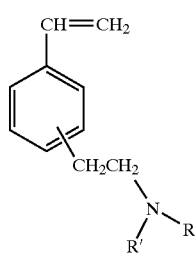

(c)

wherein R and R' can be the same or different and represent allyl groups or alkoxy groups containing from about 1 to about 10 carbon atoms;

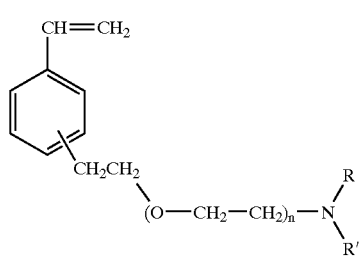

(d)

wherein n represents an integer from 1 to about 10, and wherein R and R' can be the same or different and represent alkyl groups containing from about 1 to about 10 carbon atoms;

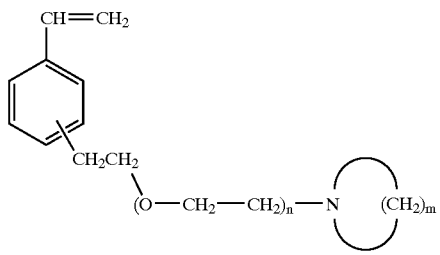

(e)

wherein n represents-an integer from 1 to about 10 and wherein m represents an integer from 4 to about 10;

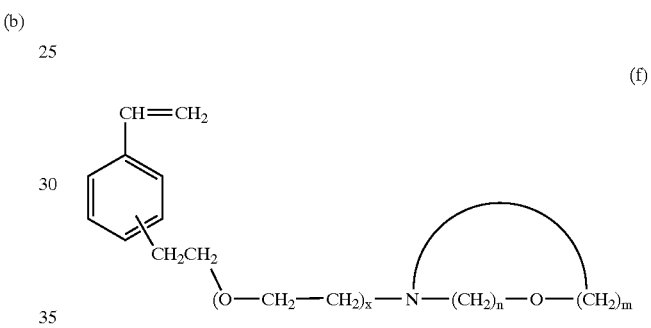

(f)

wherein x represents an integer from about 1 to about 10, wherein n represents an integer from 0 to about 10 and wherein m represents an integer from 0 to about 10, with the proviso that the sum of n and m is at least 4;

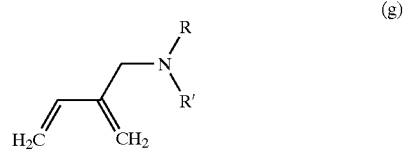

(g)

wherein R and R' can be the same or different and represent alkyl groups containing from 1 to about 10 carbon atoms,

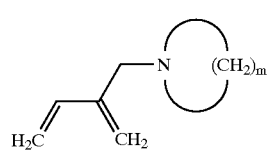

(h)

wherein m represents an integer from about 4 to about 10;

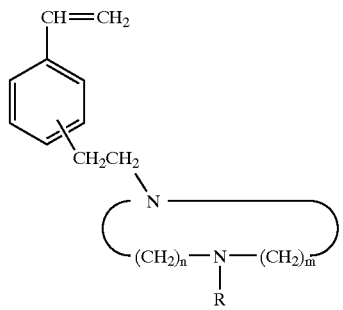

(i)

wherein R represents a hydrogen atom or an alkyl group containing from 1 to about 10 carbon atoms, wherein n represents an integer from 0 to about 10, and wherein m represents an integer from 0 to about 10, with the proviso that the sum of n and m is at least 4; and and

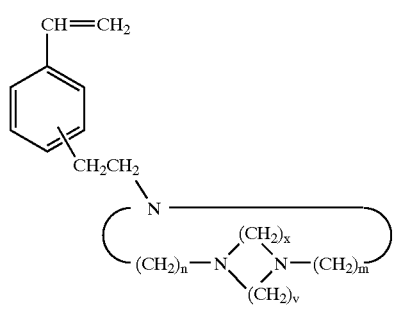

(j)

wherein n represents an integer from 0 to about 10, wherein m represents an integer from 0 to about 10, wherein x represents an integer from 1 to about 10, and wherein y represents an integer from 1 to about 10.

The present invention further discloses a process for synthesizing an amino methyl styrene monomer which comprises: (1) reacting divinyl benzene with a cyclic amine in a reacting mixture in the presence of an alkyl lithium compound at a temperature which is within the range of −80° C. to 80° C. to produce the amino ethyl styrene; and (2) deactivating the alkyl lithium compound by adding an alcohol or water to the reaction mixture containing the amino ethyl styrene. This process is preferable conducted at a temperature which is within the range of about −20° C. to about 50° C. and is most preferable conducted at a temperature is within the range of about −10° C. to about 25° C. The alkyl lithium compound is typically present at a level which is within the range of about 0.5 mole percent to about 5 mole percent, based upon the molar amount of cyclic amine present. The alkyl lithium compound is preferably present at a level which is within the range of about 1 mole percent to about 4 mole percent and is more preferably present at a level which is within the range of about 1.5 mole percent to about 2.5 mole percent, based upon the molar amount of cyclic amine present.

DETAILED DESCRIPTION OF THE INVENTION

The functionalized monomers of this invention can be copolymerized into virtually any type of synthetic rubber. In most cases the functionalized monomer will be copolymerized with at least one conjugated diolefin monomer. Optionally, other monomers that are copolymerizable with conjugated diolefin monomers, such as vinyl aromatic monomers, can also be included in the polymerization. In any case, typically from about 0.1 phm (parts by weight by 100 parts by weight of monomers) to about 100 phm of the functionalized monomer will be included in the polymerization. More typically, from about 0.05 phm to about 10 phm of the functionalized monomer will be included in the rubbery polymer. Good results can normally be attained by including 0.1 phm to 5 phm of the functionalized monomer in the rubbery polymer.

According to this invention, polymerization and recovery of polymer are suitably carried out according to various methods suitable for diene monomer polymerization processes. This includes batchwise, semi-continuous, or continuous operations under conditions that exclude air and other atmospheric impurities, particularly oxygen and moisture. The polymerization of the functionalized monomers of the invention may also be carried out in a number of different polymerization reactor systems, including but not limited to bulk polymerization, vapor phase polymerization, solution polymerization, suspension polymerization, emulsion polymerization, and precipitation polymerization systems. The commercially preferred methods of polymerization are solution polymerization and emulsion polymerization.

The polymerization reaction may use a free radical initiator, a redox initiator, an anionic initiator, a cationic initiator, or a Zeigler-Natta catalyst system. The preferred initiation system depends upon the particular monomers being polymerized and the desired characteristics of the rubbery polymer being synthesized. In emulsion polymerizations free radical initiators are typically utilized. In solution polymerizations Zeigler-Natta catalyst systems or anionic initiators, such as alkyl lithium compounds, are typically employed to initiate the polymerization. An advantage of free radical polymerization is that reactions can typically be carried out under less rigorous conditions than ionic polymerizations. Free radical initiation systems also exhibit a greater tolerance of trace impurities.

Examples of free radical initiators that are useful in the practice of the present invention are those known as "redox" initiators, such as combinations of chelated iron salts, sodium formaldehyde sulfoxylate, and organic hydroperoxides. Representative of organic hydroperoxides are cumene hydroperoxide, paramenthane hydroperoxide, and tertiary butyl hydroperoxide. Tertiary butyl hydroperoxide (t-BHP), tertiary butyl peracetate (t-BPA) and "azo" initiators, such as azobisiobutyronitrile (AIBN), are preferred.

The reaction temperature is typically maintained in the range of 0° C. to 150° C. Temperatures between about 20 and 80° C. are generally preferred. The reaction pressure is not critical. It is typically only sufficiently high to maintain liquid phase reaction conditions; it may be autogenic pressure, which-will vary depending upon the components of the reaction mixture and the temperature, or it may be higher, e.g., up to 1000 psi.

In batch operations, the polymerization time of functionalized diene monomers can be varied as desired; it may vary, for example, from a few minutes to several days. Polymerization in batch processes may be terminated when monomer is no longer absorbed, or earlier, if desired, e.g., if the reaction mixture becomes too viscous. In continuous operations, the polymerization mixture may be passed through a reactor of any suitable design. The polymerization reactions in such cases are suitably adjusted by varying the residence time. Residence times vary with the type of reactor system and range, for example, from 10 to 15 minutes to 24 or more hours.

The concentration of monomer in the reaction mixture may vary upward from 5 percent by weight of the reaction mixture, depending on the conditions employed; the range from 20 to 80 percent by weight is preferred.

The polymerization reactions according to this invention may be carried out in a suitable solvent that is liquid under the conditions of reaction and relatively inert. The solvent may have the same number of carbon atoms per molecule as the diene reactant or it may be in a different boiling range. Preferred as solvents are alkane and cycloalkane hydrocarbons. Suitable solvents are, for example, hexane, cyclohexane, methylcyclohexane, or various saturated hydrocarbon mixtures. Aromatic hydrocarbons such as benzene, toluene, isopropylbenzene, xylene, or halogenated aromatic compounds such as chlorobenzene, bromobenzene, or orthodichlorobenzene may also be employed. Other useful solvents include tetrahydrofuran and dioxane.

Conventional emulsion recipes may also be employed with the present invention; however, some restrictions and modifications may arise either from the polymerizable monomer itself, or the polymerization parameters. Ionic surfactants, known in the art, including sulfonate detergents and carboxylate, sulfate, and phosphate soaps are useful in this invention. The level of ionic surfactant is computed based upon the total weight of the organic components and may range from about 2 to 30 parts by weight of ionic surfactant per 100 parts by weight of organic components.

Preferably the polymerization is carried out to complete functionalized diene monomer conversion in order to incorporate essentially all of the polymerizable functional group-bearing monomer. Incremental addition, or a chain transfer agent, may be used in order to avoid excessive gel formation. Such minor modifications are within the skill of the artisan. After the polymerization is complete, the polymer is recovered from a slurry or solution of the polymer. A simple filtration may be adequate to separate polymer from diluent. Other means for separating polymer from diluent may be employed. The polymer may be treated, separately or while slurried in the reaction mixture, in order to separate residues. Such treatment may be with alcohols such as methanol, ethanol, or isopropanol, with acidified alcohols, or with other similar polar liquids. In many cases the polymers are obtained in hydrocarbon solutions and the polymer can be recovered by coagulation with acidified alcohol, e.g., rapidly stirred methanol or isopropanol containing 2% hydrochloric acid. Following this initial coagulation, the polymers may be washed several more times in methanol.

The functionalized diene monomers according to the present invention may also be polymerized with one or more comonomers. Some adjustments in the polymerization recipe or reaction conditions may be necessary to obtain a satisfactory rate of polymer formation, depending on the amount of functionalized monomer included and the other monomers involved. Examples of comonomers that are useful in the practice of this invention are diene monomers such as butadiene, isoprene, and hexadienes. One may, in addition to the diene monomers, use a vinyl monomer such as styrene, α-methylstyrene, divinyl benzene, vinyl chloride, vinyl acetate, vinylidene chloride, methyl methacrylate, ethyl acrylate, vinylpyridine, acrylonitrile, methacrylonitrile, methacrylic acid, itaconic acid and acrylic acid. Mixtures of different functionalized monomers and mixtures of different comonomers may be used. The monomer charge ratio by weight is normally from about 0.10/99.9 to 99.9/0.10 functionalized monomer to comonomer (including any additional vinyl monomer). A charge ratio by weight of about 5/95 to about 80/20 is preferred with 10/90 to 40/60 the most preferred. According to one embodiment, the weight ratio of functionalized diene monomer to diene monomer to vinyl monomer may range from 5:75:20 to 95:5:0. Ratios will vary depending on the amount of chemical functionality desired to be incorporated and on the reactivity ratios of the monomers in the particular polymerization system used.

The functionalized monomers of this invention offer a unique ability to randomly copolymerize with conjugated diolefin monomers in solution polymerizations that are conducted at temperatures of 20° C. or higher. The functionalized monomers of this invention can be incorporated into virtually any type of rubbery polymer that is capable of being made by solution polymerization with an anionic initiator or Zeigler-Natta type of catalyst. The polymerization employed in synthesizing the rubbery polymers will normally be carried out in a hydrocarbon solvent. Such hydrocarbon solvents are comprised of one or more aromatic, paraffinic or cycloparaffinic compounds. These solvents will normally contain from about 4 to about 10 carbon atoms per molecule and will be liquid under the conditions of the polymerization. Some representative examples of suitable organic solvents include pentane, isooctane, cyclohexane, methylcyclohexane, isohexane, n-heptane, n-octane, n-hexane, benzene, toluene, xylene, ethylbenzene, diethylbenzene, isobutylbenzene, petroleum ether, kerosene, petroleum spirits, petroleum naphtha, and the like, alone or in admixture.

In the solution polymerization, there will normally be from 5 to 30 weight percent monomers in the polymerization medium. Such polymerization media are, of course, comprised of the organic solvent and monomers. In most cases, it will be preferred for the polymerization medium to contain from 10 to 25 weight percent monomers. It is generally more preferred for the polymerization medium to contain 15 to 20 weight percent monomers.

The synthetic rubbers made by the process of this invention can be made by random copolymerization of the functionalized monomer with a conjugated diolefin monomer or by the random terpolymerization of the functionalized monomer with a conjugated diolefin monomer and a vinyl aromatic monomer. It is, of course, also possible to make such rubbery polymers by polymerizing a mixture of conjugated diolefin monomers with one or more ethylenically unsaturated monomers, such as vinyl aromatic monomers. The conjugated diolefin monomers which can be utilized in the synthesis of rubbery polymers which can be coupled in accordance with this invention generally contain from 4 to 12 carbon atoms. Those containing from 4 to 8 carbon atoms are generally preferred for commercial purposes. For similar reasons, 1,3-butadiene and isoprene are the most commonly utilized conjugated diolefin monomers. Some additional conjugated diolefin monomers that can be utilized include 2,3-dimethyl-1,3-butadiene, piperylene, 3-butyl-1,3-octadiene, 2-phenyl-1,3-butadiene, and the like, alone or in admixture.

Some representative examples of ethylenically unsaturated monomers that can potentially be polymerized into rubbery polymers that contain the functionalized monomers of this invention include alkyl acrylates, such as methyl acrylate, ethyl acrylate, butyl acrylate, methyl methacrylate and the like; vinylidene monomers having one or more terminal $CH_2=CH-$ groups; vinyl aromatics such as styrene, α-methylstyrene, bromostyrene, chlorostyrene, fluorostyrene and the like; α-olefins such as ethylene, propylene, 1-butene and the like; vinyl halides, such as vinylbromide, chloroethane (vinylchloride), vinylfluoride, vinyliodide, 1,2-dibromoethene, 1,1-dichloroethene (vinylidene chloride), 1,2-dichloroethene and the like; vinyl esters, such as vinyl acetate; α,β-olefinically unsaturated nitriles, such as acrylonitrile and methacrylonitrile; α,β-olefinically unsaturated amides, such as acrylamide, N-methyl acrylamide, N,N-dimethylacrylamide, methacrylamide and the like.

Rubbery polymers which are copolymers of one or more diene monomers with one or more other ethylenically unsaturated monomers will normally contain from about 50 weight percent to about 99 weight percent conjugated diolefin monomers and from about 1 weight percent to about 50 weight percent of the other ethylenically unsaturated monomers in addition to the conjugated diolefin monomers. For example, copolymers of conjugated diolefin monomers with vinylaromatic monomers, such as styrene-butadiene rubbers which contain from 50 to 95 weight percent conjugated diolefin monomers and from 5 to 50 weight percent vinylaromatic monomers, are useful in many applications.

Vinyl aromatic monomers are probably the most important group of ethylenically unsaturated monomers which are commonly incorporated into polydiene rubbers. Such vinyl aromatic monomers are, of course, selected so as to be copolymerizable with the conjugated diolefin monomers being utilized. Generally, any vinyl aromatic monomer which is known to polymerize with organolithium initiators can be used. Such vinyl aromatic monomers typically contain from 8 to 20 carbon atoms. Usually, the vinyl aromatic monomer will contain from 8 to 14 carbon atoms. The most widely used vinyl aromatic monomer is styrene. Some examples of vinyl aromatic monomers that can be utilized include styrene, 1-vinylnaphthalene, 2-vinylnaphthalene, α-methylstyrene, 4-phenylstyrene, 3-methylstyrene and the like.

Some representative examples of rubbery polymers that can be functionalized with the functionalized monomers of this invention include polybutadiene, polyisoprene, styrene-butadiene rubber (SBR), α-methylstyrene-butadiene rubber, α-methylstyrene-isoprene rubber, styrene-isoprene-butadiene rubber (SIBR), styrene-isoprene rubber (SIR), isoprene-butadiene rubber (IBR), α-methylstyrene-isoprene-butadiene rubber and α-methylstyrene-styrene-isoprene-butadiene rubber. In cases where the rubbery polymer is comprised of repeat units that are derived from two or more monomers, the repeat units which are derived from the different monomers, including the functiopnalized monomers, will normally be distributed in an essentially random manner. The repeat units that are derived from the monomers differ from the monomer in that a double bond is normally consumed in by the polymerization reaction.

The rubbery polymer can be made by solution polymerization in a batch process by in a continuous process by continuously charging at least one conjugated diolefin monomer, the functionalized monomer, and any additional monomers into a polymerization zone. The polymerization zone will typically be a polymerization reactor or a series of polymerization reactors. The polymerization zone will normally provide agitation to keep the monomers, polymer, initiator, and modifier well dispersed throughout the organic solvent the polymerization zone. Such continuous polymerizations are typically conducted in a multiple reactor system. The rubbery polymer synthesized is continuously withdrawn from the polymerization zone. The monomer conversion attained in the polymerization zone will normally be at least about 85 percent. It is preferred for the monomer conversion to be at least about 90 percent.

The polymerization will be initiated with an anionic initiator, such as an alkyl lithium compound, or a Zeigler-Natta catalyst. The alkyl lithium compounds that can be used will typically contain from 1 to about 8 carbon atoms, such as n-butyl lithium, The amount of the lithium initiator utilized will vary with the monomers being polymerized and with the molecular weight that is desired for the polymer being synthesized. However, as a general rule, from 0.01 to 1 phm (parts per 100 parts by weight of monomer) of the lithium initiator will be utilized. In most cases, from 0.01 to 0.1 phm of the lithium initiator will be utilized with it being preferred to utilize 0.025 to 0.07 phm of the lithium initiator.

The polymerization process of this invention is normally conducted in the presence of polar modifiers, such as alkyltetrahydrofurfuryl ethers. Some representative examples of specific polar modifiers that can be used include methyltetrahydrofurfuryl ether, ethyltetrahydrofurfuryl ether, propyltetrahydrofurfuryl ether, butyltetrahydrofurfuryl ether, hexyltetrahydrofurfuryl ether, octyltetrahydrofurfuryl ether, dodecyltetrahydrofurfuryl ether, diethyl ether, di-n-propyl ether, diisopropyl ether, di-n-butyl ether, tetrahydrofuran, dioxane, ethylene glycol dimethyl ether, ethylene glycol diethyl ether, diethylene glycol dimethyl ether, diethylene glycol diethyl ether, triethylene glycol dimethyl ether, trimethylamine, triethylamine, N,N,N',N'-tetramethylethylenediamine, N-methyl morpholine, N-ethyl morpholine, or N-phenyl morpholine.

The polar modifier will typically be employed at a level wherein the molar ratio of the polar modifier to the lithium initiator is within the range of about 0.01:1 to about 5:1. The molar ratio of the polar modifier to the lithium initiator will more typically be within the range of about 0.1:1 to about 4:1. It is generally preferred for the molar ratio of polar modifier to the lithium initiator to be within the range of about 0.25:1 to about 3:1. It is generally most preferred for the molar ratio of polar modifier to the lithium initiator to be within the range of about 0.5:1 to about 3:2.

The polymerization can optionally be conducted utilizing an oligomeric oxolanyl alkane as the modifier. Such oligomeric oxolanyl alkanes will typically be of a structural formula selected from the group consisting of:

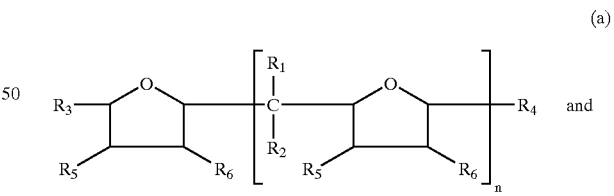

(a)

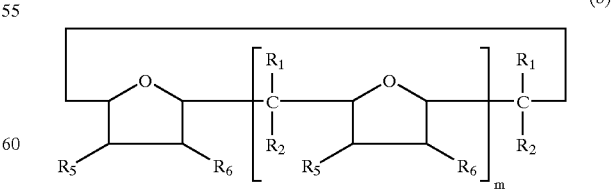

(b)

wherein n represents an integer from 1 to 5, wherein m represents an integer from 3 to 5, wherein $R_1$, $R_2$, $R_3$, $R_4$, $R_5$, and $R_6$ can be the same or different, and wherein $R_1$, $R_2$, $R_3$, $R_4$, $R_5$, and $R_6$ represent a member selected from the group consisting of hydrogen atoms and alkyl groups containing from 1 to about 8 carbon atoms. It is typically preferred for $R_1$, $R_2$, $R_3$, $R_4$, $R_5$, and $R_6$ represent a member selected from the group consisting of hydrogen atoms and alkyl groups containing from 1 to 4 carbon atoms.

The polymerization temperature utilized can vary over a broad range of from about −20° C. to about 180° C. In most cases, a polymerization temperature within the range of about 30° C. to about 125° C. will be utilized. It is typically preferred for the polymerization temperature to be within the range of about 45° C. to about 100° C. It is typically most preferred for the polymerization temperature to be within the range of about 60° C. to about 90° C. The pressure used will normally be sufficient to maintain a substantially liquid phase under the conditions of the polymerization reaction.

The polymerization is conducted for a length of time sufficient to permit substantially complete polymerization of monomers. In other words, the polymerization is normally carried out until high conversions of at least about 85 percent are attained. The polymerization is then terminated by the addition of an agent, such as an alcohol, a terminating agent, or a coupling agent. For example, a tin halide and/or silicon halide can be used as a coupling agent. The tin halide and/or the silicon halide are continuous added in cases where asymmetrical coupling is desired. This continuous addition of tin coupling agent and/or the silicon coupling agent is normally done in a reaction zone separate from the zone where the bulk of the polymerization is occurring. The coupling agents will normally be added in a separate reaction vessel after the desired degree of conversion has been attained. The coupling agents can be added in a hydrocarbon solution, e.g., in cyclohexane, to the polymerization admixture with suitable mixing for distribution and reaction. In other words, the coupling will typically be added only after a high degree of conversion has already been attained. For instance, the coupling agent will normally be added only after a monomer conversion of greater than about 85 percent has been realized. It will typically be preferred for the monomer conversion to reach at least about 90 percent before the coupling agent is added.

The tin halides used as coupling agents will normally be tin tetrahalides, such as tin tetrachloride, tin tetrabromide, tin tetrafluoride or tin tetraiodide. However, tin trihalides can also optionally be used. Polymers coupled with tin trihalides having a maximum of three arms. This is, of course, in contrast to polymers coupled with tin tetrahalides which have a maximum of four arms. To induce a higher level of branching, tin tetrahalides are normally preferred. As a general rule, tin tetrachloride is most preferred.

The silicon coupling agents that can be used will normally be silicon tetrahalides, such as silicon tetrachloride, silicon tetrabromide, silicon tetrafluoride or silicon tetraiodide. However, silicon trihalides can also optionally be used. Polymers coupled with silicon trihalides having a maximum of three arms. This is, of course, in contrast to polymers coupled with silicon tetrahalides which have a maximum of four arms. To induce a higher level of branching, silicon tetrahalides are normally preferred. As a general rule, silicon tetrachloride is most preferred of the silicon coupling agents.

A combination of a tin halide and a silicon halide can optionally be used to couple the rubbery polymer. By using such a combination of tin and silicon coupling agents improved properties for tire rubbers, such as lower hysteresis, can be attained. It is particularly desirable to utilize a combination of tin and silicon coupling agents in tire tread compounds that contain both silica and carbon black. In such cases, the molar ratio of the tin halide to the silicon halide employed in coupling the rubbery polymer will normally be within the range of 20:80 to 95:5. The molar ratio of the tin halide to the silicon halide employed in coupling the rubbery polymer will more typically be within the range of 40:60 to 90:10. The molar ratio of the tin halide to the silicon halide employed in coupling the rubbery polymer will preferably be within the range of 60:40 to 85:15. The molar ratio of the tin halide to the silicon halide employed in coupling the rubbery polymer will most preferably be within the range of 65:35 to 80:20.

Broadly, and exemplary, a range of about 0.01 to 4.5 milliequivalents of tin coupling agent (tin halide and silicon halide) is employed per 100 grams of the rubbery polymer. It is normally preferred to utilize about 0.01 to about 1.5 milliequivalents of the coupling agent per 100 grams of polymer to obtain the desired Mooney viscosity. The larger quantities tend to result in production of polymers containing terminally reactive groups or insufficient coupling. One equivalent of tin coupling agent per equivalent of lithium is considered an optimum amount for maximum branching. For instance, if a mixture tin tetrahalide and silicon tetrahalide is used as the coupling agent, one mole of the coupling agent would be utilized per four moles of live lithium ends. In cases where a mixture of tin trihalide and silicon trihalide is used as the coupling agent, one mole of the coupling agent will optimally be utilized for every three moles of live lithium ends. The coupling agent can be added in a hydrocarbon solution, e.g., in cyclohexane, to the polymerization admixture in the reactor with suitable mixing for distribution and reaction.

After the coupling has been completed, a tertiary chelating alkyl 1,2-ethylene diamine or a metal salt of a cyclic alcohol can optionally be added to the polymer cement to stabilize the coupled rubbery polymer. The tertiary chelating amines that can be used are normally chelating alkyl diamines of the structural formula:

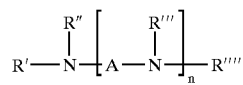

wherein n represents an integer from 1 to about 6, wherein A represents an alkylene group containing from 1 to about 6 carbon atoms and wherein R', R", R'" and R"" can be the same or different and represent alkyl groups containing from 1 to about 6 carbon atoms. The alkylene group A is of the formula $-(-CH_2-)_m$ wherein m is an integer from 1 to about 6. The alkylene group will typically contain from 1 to 4 carbon atoms (m will be 1 to 4) and will preferably contain 2 carbon atoms. In most cases, n will be an integer from 1 to about 3 with it being preferred for n to be 1. It is preferred for R', R", R'" and R"" to represent alkyl groups which contain from 1 to 3 carbon atoms. In most cases, R', R", R'" and R"" will represent methyl groups.

In most cases, from about 0.01 phr (parts by weight per 100 parts by weight of dry rubber) to about 2 phr of the chelating alkyl 1,2-ethylene diamine or metal salt of the cyclic alcohol will be added to the polymer cement to stabilize the rubbery polymer. Typically, from about 0.05 phr to about 1 phr of the chelating alkyl 1,2-ethylene diamine or metal salt of the cyclic alcohol will be added. More typically, from about 0.1 phr to about 0.6 phr of the chelating alkyl 1,2-ethylene diamine or the metal salt of the cyclic alcohol will be added to the polymer cement to stabilize the rubbery polymer.

The terminating agents that can be used to stop the polymerization and to "terminate" the living rubbery polymer include tin monohalides, silicon monohalides, N,N,N', N'-tetradialkyldiamino-benzophenones (such as tetramethyldiaminobenzophenone and the like), N,N-dialkylaminobenzaldehydes (such as dimethylaminobenzaldehyde and the like),1,3-dialkyl-2-imidazolidinones (such as 1,3-dimethyl-2-imidazolidinone and the like), 1-alkyl substituted pyrrolidinones; 1-aryl substituted pyrrolidinones, dialkyl-dicycloalkyl-carbodiimides containing from about 5 to about 20 carbon atoms, and dicycloalkyl-carbodiimides containing from about 5 to about 20 carbon atoms.

After the termination step, and optionally the stabilization step, has been completed, the rubbery polymer can be recovered from the organic solvent. The coupled rubbery polymer can be recovered from the organic solvent and residue by means such as chemical (alcohol) coagulation, thermal desolventization, or other suitable method. For instance, it is often desirable to precipitate the rubbery polymer from the organic solvent by the addition of lower alcohols containing from about 1 to about 4 carbon atoms to the polymer solution. Suitable lower alcohols for precipitation of the rubber from the polymer cement include methanol, ethanol, isopropyl alcohol, normal-propyl alcohol and t-butyl alcohol. The utilization of lower alcohols to precipitate the rubbery polymer from the polymer cement also "terminates" any remaining living polymer by inactivating lithium end groups. After the coupled rubbery polymer is recovered from the solution, steam-stripping can be employed to reduce the level of volatile organic compounds in the coupled rubbery polymer. Additionally, the organic solvent can be removed from the rubbery polymer by drum drying, extruder drying, vacuum drying, and the like.

The polymers of the present invention can be used alone or in combination with other elastomers to prepare an rubber compounds, such as a tire treadstock, sidewall stock or other tire component stock compounds. In a tire of the invention, at least one such component is produced from a vulcanizable elastomeric or rubber composition. For example, the rubbery polymer made by the process of this invention can be blended with any conventionally employed treadstock rubber which includes natural rubber, synthetic rubber and blends thereof. Such rubbers are well known to those skilled in the art and include synthetic polyisoprene rubber, styrene/butadiene rubber (SBR), polybutadiene, butyl rubber, Neoprene, ethylene/propylene rubber, ethylene/propylene/diene rubber (EPDM), acrylonitrile/butadiene rubber (NBR), silicone rubber, the fluoroelastomers, ethylene acrylic rubber, ethylene vinyl acetate copolymer (EVA), epichlorohydrin rubbers, chlorinated polyethylene rubbers, chlorosulfonated polyethylene rubbers, hydrogenated nitrile rubber, tetrafluoroethylene/propylene rubber and the like.

When the rubbery polymers made by the process of the present invention are blended with conventional rubbers, the amounts can vary widely such as between 10 and 99 percent by weight. In any case, tires made with synthetic rubbers that are synthesized utilizing the technique of this invention exhibit decreased rolling resistance. The greatest benefits are realized in cases where the tire tread compound is made with the rubbery polymer synthesized utilizing the technique of this invention. However, benefits can also by attained in cases where at least one structural element of the tire, such as subtread, sidewalls, body ply skim, or bead filler, is comprised of the rubbery.

The synthetic rubbers made in accordance with this invention can be compounded with carbon black in amounts ranging from about 5 to about 100 phr (parts by weight per 100 parts by weight of rubber), with about 5 to about 80 phr being preferred, and with about 40 to about 70 phr being more preferred. The carbon blacks may include any of the commonly available, commercially-produced carbon blacks but those having a surface area (EMSA) of at least 20 $m^2/g$ and more preferably at least 35 $m^2/g$ up to 200 $m^2/g$ or higher are preferred. Surface area values used in this application are those determined by ASTM test D-1765 using the cetyltrimethyl-ammonium bromide (CTAB) technique. Among the useful carbon blacks are furnace black, channel blacks and lamp blacks. More specifically, examples of the carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks which may be utilized include acetylene blacks. Mixtures of two or more of the above blacks can be used in preparing the carbon black products of the invention. Typical values for surface areas of usable carbon blacks are summarized in the following table.

| Carbon Black | |
|---|---|
| ASTM Designation (D-1765-82a) | Surface Area (D-3765) |
| N-110 | 126 $m^2/g$ |
| N-220 | 111 $m^2/g$ |
| N-330 | 83 $m^2/g$ |
| N-339 | 95 $m^2/g$ |
| N-550 | 42 $m^2/g$ |
| N-660 | 35 $m^2/g$ |

The carbon blacks utilized in the preparation of rubber compounds may be in pelletized form or an unpelletized flocculent mass. Preferably, for more uniform mixing, unpelletized carbon black is preferred. The reinforced rubber compounds can be cured in a conventional manner with about 0.5 to about 4 phr of known vulcanizing agents. For example, sulfur or peroxide-based curing systems may be employed. For a general disclosure of suitable vulcanizing agents one can refer to Kirk-Othmer, Encyclopedia of Chemical Technology, 3rd ed., Wiley Interscience, N.Y. 1982, Vol. 20, pp. 365–468, particularly "Vulcanization Agents and Auxiliary Materials" pp. 390–402. Vulcanizing agents can, of curse, be used alone or in combination. Vulcanizable elastomeric or rubber compositions can be prepared by compounding or mixing the polymers thereof with carbon black and other conventional rubber additives such as fillers, plasticizers, antioxidants, curing agents and the like, using standard rubber mixing equipment and procedures and conventional amounts of such additives.

The functionalized styrene monomer can be synthesized (1) reacting a secondary amine with an organolithium compound to produce a lithium amide, and (2) reacting the lithium amide with divinylbenzene or diisopropenyl benzene to produce the functionalized styrene monomer. This procedure can be depicted as follows:

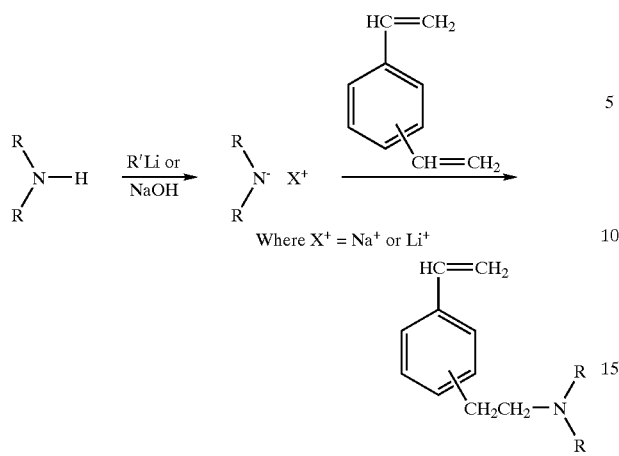

A process for synthesizing an amino ethyl styrene monomer which comprises: (1) reacting divinyl benzene with a cyclic amine in a reacting mixture in the presence of an alkyl lithium compound at a temperature which is within the range of –80° C. to 80° C. to produce the amino ethyl styrene; and (2) deactivating the alkyl lithium compound by adding an alcohol or water to the reaction mixture containing the amino ethyl styrene.

Functionalized monomers that contain cyclic amines can also be made by the same reaction scheme wherein a cyclic secondary amine is employed in the first step of the reaction. This reaction scheme can be depicted as follows:

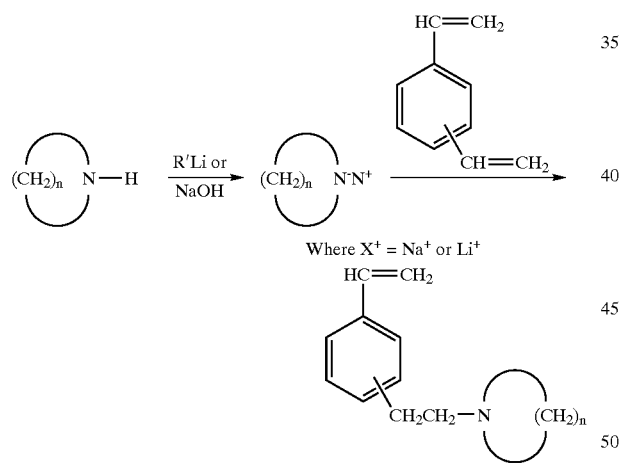

In another embodiment of this invention a functionalized monomer can be synthesized by a process that comprises (1) reacting a secondary amine with a 2,3-dihalopropene to produce a vinyl halide containing secondary amine having a structural formula selected from the group consisting of (a)

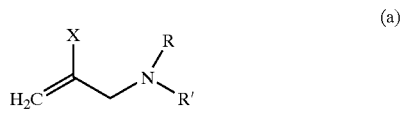

wherein R and R' can be the same or different and represent allyl, alkoxyl or alkyl groups containing from 1 to about 10 carbon atoms, and wherein X represents a halogen atom, and

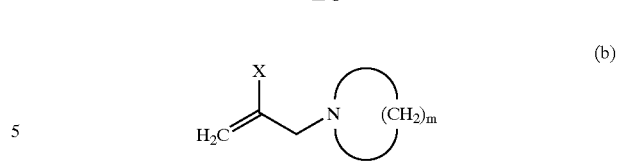

wherein m represents an integer from 4 to about 10, and wherein X represents a halogen atom; and (2) reacting the vinyl halide containing secondary amine with a vinyl magnesium halide to produce the monomer, wherein the monomer has a structural formula selected from the group consisting of (a)

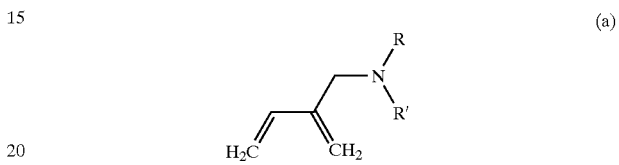

wherein R and R' can be the same or different and represent allyl, alkoxyl or alkyl groups containing from 1 to about 10 carbon atoms, and (b)

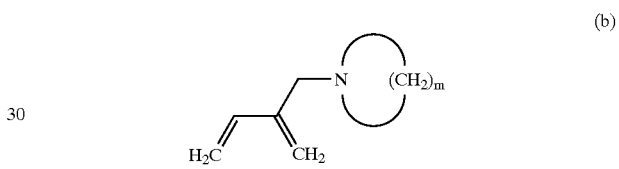

wherein m represents an integer from about 4 to about 10. Such a reaction scheme can be depicted as follows:

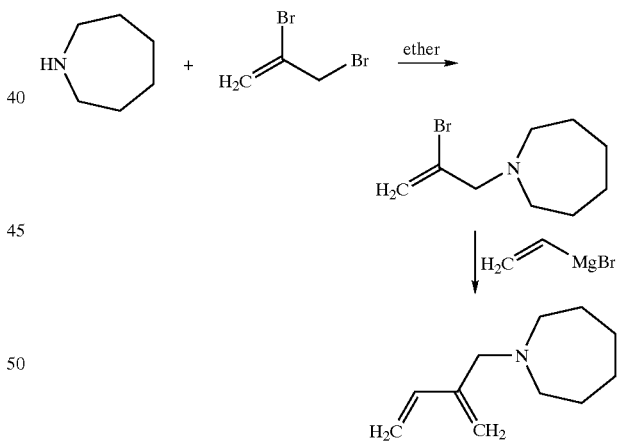

In the first step of this reaction scheme a secondary cyclic amine is reacted with a 2,3-dihalopropene (2,3-bromopropene is shown above). This step is-typically conducted in an organic solvent, such as diethyl ether, at a temperature which is within the range of about –20° C. to about 60° C., and is preferable conducted at a temperature which is within the range of 0° C. to about 30° C. As can be seen this results in the production of a vinyl halide containing secondary amine.

In the second step of the process the vinyl halide containing secondary amine is reacted with a vinyl magnesium halide to produce the functionalized monomer. The second step is conducted in a polar organic solvent, such as tetrahydrofuran or diethyl ether. The second step is also conducted at a temperature that is within the range of about −20° C. to about 60° C., and is preferable conducted at a temperature which is within the range of 0° C. to about 30° C.

This invention is illustrated by the following examples that are merely for the purpose of illustration and are not to be regarded as limiting the scope of the invention or the manner in which it can be practiced. Unless specifically indicated otherwise, parts and percentages are given by weight.

EXAMPLE 1

In this experiment 2-(N-hexamethyleneimino)-methyl 1,3-butadiene was synthesized utilizing the technique of this invention. In the procedure used a solution of 2,3-dibromopropane (0.1 mol) in ethyl ether was slowly added to a solution of hexamethyleneimine (0.4 mol) in ethyl ether at 0° C. The reaction mixture was stirred overnight at room temperature. The next day a 1M NaOH solution was added to quench the mixture and the organic layer was collected using a separatory funnel and-extracted with diethyl ether. The organic layer was subsequently washed with water two times. After drying with sodium sulfate, the filtrate was evaporated and the resulting residue was distilled to yield 2-bromo-3-(N-hexamethyleneimino)propene. The boiling point and yield of the product were determined to be 65–68° C. at 30 mm-Hg. The yield was determined to be 60%. The molecular structure of 2-bromo-3-(N-hexamethylene-imino) propene was verified by proton NMR.

Vinyl magnesium bromide in tetrahydrofuran (THF; 0.085 mol) was added dropwise to a flask containing the 2-bromo-3-(N-hexamethylene-imino)propene (0.056 mol) in the presence of [1,3-bis(diphenylphosphino) propane] dichloronickel(II) (0.21 mol) at 0° C. After stirring for 24 hours at room temperature, the hydrolysis of the reaction mixture by saturated ammonium chloride solution was carried out and followed by extraction with diethyl ethyl three times. The organic material was dried by sodium sulfate and then filtered. After evaporating the solvent, the residue was distilled to give a colorless liquid of 2-(N-hexa-methyleneimino)-methyl 1,3-butadiene. The boiling point and yield were −114° C. at 30 mm-Hg and 60%, respectively. The molecular structure of the resulting product was verified by proton NMR.

EXAMPLE 2

The preparation of 2-(N,N-diethylamino)-methyl-1,3-butadiene is described in this example. The procedure described in Example 1 was utilized except that N,N-diethylamine was used in place of hexamethyleneimine. The yield for the intermediate product, 2-bromo-3-(N,N-diethylamino)propene was 98%. The boiling point and yield of the final product, 2-(N,N-diethylamino)-methyl-1,3-butadine was determined to be 112–114° C. at 30 mm-Hg and 50%, respectively.

EXAMPLES 3–5

In these experiments 2-(N-pyrrolidino)-methyl-1,3-butadiene, 2-(N-morpholino)-methyl-1,3-butadiene, and 2-(N-piperidino)-methyl-1,3-butadiene were synthesized utilizing a procedure that is similar to the one described in Example 1 except that pyrrolidine, morpholine and piperidine were used in place of the hexamethyleneimine.

EXAMPLE 6

In this experiment, a 25/75 SBR containing 1% of hex-amethyleneimine (HMI) functional groups was prepared. 2350 g of a silica/alumina/molecular sieve dried premix containing 19.50 weight percent styrene and 1,3-butadiene in hexanes was charged into a one-gallon (3.8 liters) reactor. The styrene to 1,3-butadiene ratio was 25:75. 4.6 grams of a neat 2-(N-hexamethyleneimino)-methyl 1,3-butadiene was added to the reactor. Then, 2.9 ml of 1 M solution of N,N,N',N'-tetramethyethylenediamine (TMEDA) and 2.3 ml of 1.6 M n-butyl lithium (n-BuLi) in hexanes were added to the reactor, respectively. The polymerization was carried out at 70° C. for 90 minutes. The GC analysis of the residual monomer contained in the polymerization mixture indicated that the all monomers were consumed at this time, the polymer cement was then shortstopped with ethanol and then removed from the reactor and stabilized with 1 phm of antioxidant. After evaporating hexanes, the resulting polymer was dried in a vacuum oven at 50° C.

The styrene-butadiene rubber (SBR) produced was determined to have a glass transition temperature (Tg) at −33° C. It was also determined to have a microstructure which contained 41 percent 1,2-polybutadiene units, 34 percent 1,4-polybutadiene units and 25 percent random polystyrene units. It also contained about 1 weight percent of HMI units. The Mooney viscosity (ML-4) at 100° C. for this SBR was determined to be 27. The GPC data of this polymer was also determined to have a Mn of 129,000 and Mw of 136,000. The polydispersity (Mw/Mn) was 1.05. The HMI functionality of the resulting SBR was verified via a HPLC-GPEC (Gradient polymer elution chromatography) method using Novapak C18 column using a mixture of acetonitrile/THF as solvent. As determined by GPEC method, 93% of this polymer contains HMI functional groups.

EXAMPLES 7–8

In these examples, 25/75 SBRs containing 0.25 and 0.5 weight percent of 2-(N-hexamethyleneimino)-methyl 1,3-butadiene were prepared using the procedures described in Example 6 except that 1.2 and 2.3 grams of 2-(N-hexamethyleneimino)-methyl 1,3-butadiene, respectively were added to the premix prior to polymerization. The characterization data of these two polymers are listed in Table 1.

EXAMPLE 9

In the example, a tin coupled 25/75 SBR containing 0.5 weight percent of 2-(N-hexamethyleneimino)-methyl 1,3-butadiene was prepared. 2350 g of a silica/alumina/ molecular sieve dried premix containing 19.50 weight percent styrene and 1,3-butadiene in hexanes was charged into a one-gallon (3.8 liters) reactor. The styrene to 1,3-butadiene ratio was 25:75. 2.3 grams of a neat 2-(N-hexamethyleneimino)-methyl 1,3-butadiene was added to the reactor. 2.9 ml of 1 M solution of N,N,N', N'-tetramethyethylenediamine (TMEDA) and 2.3 ml of 1.6 M n-butyl lithium (n-BuLi) in hexanes were added to the reactor, respectively. The polymerization was carried out at 70° C. for 90 minutes. The GC analysis of the residual monomer contained in the polymerization mixture indicated that the all monomers were consumed at this time. 0.9 ml of a 1 M solution of tin tetrachloride in hexanes was then added to the polymerization mixture. The coupling reaction was allowed to proceed at 70° C. for 30 minutes. The coupling efficiency was 69%. The characterization data of this coupled and HMI functionalized polymer are also listed in Table 1.

COMPARATIVE EXAMPLE 10

In this example, a control 25/75 SBR containing 0 weight percent of 2-(N-hexamethyleneimino)-methyl 1,3-butadiene was prepared using the procedures described in Example 6 except no 2-(N-hexamethyleneimino)-methyl 1,3-butadiene was used. The characterization data of this polymer are also included in Table 1.

polymerization mixture at 0, 5, 15, 30 and 90 minutes time periods. The total polymerization time was 100 minutes. The characterization data of this polymer are listed in Table 2.

TABLE 1

| Example No. | wt % HMI- Monomer | Coupler | Tg (° C.) | ML-4 | GPC Mn | Mw | Mw/Mn |
|---|---|---|---|---|---|---|---|
| 10 | 0 | None | −33 | 23 | 137,000 | 139,000 | 1.02 |
| 7 | 0.25 | None | −36 | 21 | 126,000 | 128,000 | 1.01 |
| 8 | 0.50 | None | −32 | 27 | 139,000 | 142,000 | 1.03 |
| 6 | 1.00 | None | −33 | 27 | 129,000 | 136,000 | 1.05 |
| 9 | 0.50 | SnCl4 | −32 | 83 | 677,000 | 812,000 | 1.20 (42%) |
|   |   |   |   |   | 329,000 | 335,000 | 1.02 (27%) |
|   |   |   |   |   | 145,000 | 155,000 | 1.06 (31%) |

EXAMPLE 11

In this example, a 25/75 SBR containing 0.5 weight percent of 2-(N-hexamethyleneimino)-methyl 1,3-butadiene was prepared using the procedures described in Example 6 except that 2.3 grams of 2-(N-hexamethyleneimino)-methyl 1,3-butadiene was pre-reacted with n-BuLi in the presence of TMEDA. The pre-reacted n-BuLi containing HMI functional groups was then used as the catalyst to initiate the polymerization. The characterization data of this polymer are listed in Table 2.

EXAMPLES 12–13

In these examples, 25/75 SBRs containing 0.1 and 0.25% weight percent of 2-(N-hexamethyleneimino)-methyl 1,3-butadiene were prepared using the procedures described in Example 11 except that 0.5 and 1.2 grams of 2-(N-hexamethyleneimino)-methyl 1,3-butadiene were pre-reacted with n-BuLi in the presence of TMEDA. The characterization data of this polymer are listed in Table 2.

EXAMPLES 15–16

In these examples, 25/75 SBRs containing 0.1 and 0.25 weight percent of 2-(N-hexamethyleneimino)-methyl 1,3-butadiene were prepared using the procedures described in Example 14 except that 0.5 and 1.2 grams of 2-(N-hexamethyleneimino)-methyl 1,3-butadiene were added sequentially to the polymerization mixture as indicated in Example 14. The characterization data of this polymer are listed in Table 2.

EXAMPLE 17

In this example, a 25/75 SBR containing 0.25 weight percent of 2-(N-hexamethyleneimino)-methyl 1,3-butadiene was prepared using the procedures described in Example 6 except that 1.2 grams of 2-(N-hexamethyleneimino)-methyl 1,3-butadiene was added to the polymerization mixture at the end of polymerization (90 minutes). The polymerization was continued for another 30 minutes at 70° C. The characterization data of this polymer are listed in Table 2.

TABLE 2

| Example No. | wt % HMI- Monomer | Mode of HMI- Monomer addition | Tg (° C.) | ML-4 | GPC Mn | Mw | Mw/Mn |
|---|---|---|---|---|---|---|---|
| 7 | 0.25 | initial charge | −36 | 21 | 126,000 | 128,000 | 1.01 |
| 8 | 0.50 | initial charge | −32 | 27 | 139,000 | 142,000 | 1.03 |
| 6 | 1.00 | initial charge | −33 | 27 | 129,000 | 136,000 | 1.05 |
| 11 | 0.50 | pre-reacted | −33 | 27 | 133,900 | 136,300 | 1.02 |
| 12 | 0.10 | pre-reacted | −33 | 26 | 136,600 | 138,800 | 1.02 |
| 13 | 0.25 | pre-reacted | −37 | 24 | 129,000 | 136,000 | 1.02 |
| 14 | 0.50 | sequential | −36 | 21 | 81,600 | 86,730 | 1.06 (50%) |
|    |      |            |     |    | 212,000 | 235,600 | 1.11 (50%) |
| 15 | 0.10 | sequential | −35 | 25 | 115,900 | 121,300 | 1.05 (80%) |
|    |      |            |     |    | 257,600 | 265,200 | 1.03 (20%) |
| 16 | 0.25 | sequential | −33 | 24 | 95,800 | 100,000 | 1.04 (57%) |
|    |      |            |     |    | 227,000 | 245,200 | 1.08 (43%) |
| 17 | 0.25 | end charge | −33 | 29 | 138,400 | 140,200 | 1.01 |

EXAMPLE 14

In this example, a 25/75 SBR containing 0.5 weight percent of 2-(N-hexamethyleneimino)-methyl 1,3-butadiene were prepared using the procedures described in Example 6 except that 4.6 grams of 2-(N-hexamethyleneimino)-methyl 1,3-butadiene was diluted with 10.8 ml of dried hexane and added sequentially in 5 equal portions (3 ml each) to the

COMPARATIVE EXAMPLE 18

In this example, a 25/75-SBR containing 2% of pyrrolidine functional groups was prepared via co-polymerizing styrene/1,3-butadiene monomers with 4-(N-pyrrolidinomethyl) styrene. The procedure described in example 6 was employed except that 9.2 grams of a neat 4-(N-pyrrolidinomethyl) styrene was used instead of 2-(N-hexamethyleneimino)-methyl 1,3-butadiene. Based on GC analysis of the residual monomer, the polymerization was also completed in 90 minutes at 70° C. The GC data also indicated that 4-(N-pyrrolidinomethyl) styrene was randomly distributed along the polymer chains.

The styrene-butadiene rubber (SBR) produced was determined to have a glass transition temperature (Tg) at −30° C. It was also determined to have a microstructure which contained 42 percent 1,2-polybutadiene units, 32 percent 1,4-polybutadiene units, 24 percent random polystyrene units and 2% 4-(N-pyrrolidino-methyl) styrene units. The Mooney viscosity (ML-4) at 100° C. for this SBR was determined to be 27. The GPC data of this polymer was also determined to have a Mn of 131,000 and Mw of 134,000. The polydispersity (Mw/Mn) was 1.02

COMPARATIVE EXAMPLES 19–20

In these examples, 25/75 SBRs containing 2 weight percent of HMI and piperidine functional groups were prepared using the procedures described in Example 18 except that 4-(N-hexamethyleneiminomethyl) styrene and 4-(N-piperidinomethyl) styrene, in place of 4-(N-pyrrolidinomethyl) styrene, were added to the premix, respectively prior to polymerization. The Tg and ML-4 of these two amine functionalized SBRs were −30° C., 26 and −31° C., 28, respectively.

EXAMPLE 21

In this example, a 25/75 SBRs containing 1 weight percent of di-allylamine functional groups was prepared using the procedures described in Example 18 except that 4-(N-diallylaminomethyl) styrene was used instead of 4-(N-pyrrolidinomethyl) styrene. The polymer was determined to have a Tg at −40° C.

EXAMPLE 22

In this experiment, a high trans 10/90 SBR containing 0.5% pyrrolidine functional groups was prepared. 2150 g of a silica/alumina/molecular sieve dried premix containing 19.50 weight percent styrene/1,3-butadiene in hexane was charged into a one-gallon (3.8 liters) reactor. 2.1 grams of 2-(N-hexamethylene-imino)-methyl 1,3-butadiene was also added to the reactor. 20 ml of a 0.172 M pre-alkylated barium catalyst (prepared by reacting one mole of barium salt of di(ethylene glycol)ethylether (BaDEGEE) in ethylbenzene with 4 moles tri-n-octylaluminum (TOA) in hexanes at 70° C.) and 7 ml of 1.6 M solution of n-butyllithium (n-BuLi) in hexanes were added to the reactor The polymerization was carried out at 100° C. for 3 hours. The GC analysis of the residual monomer contained in the polymerization mixture indicated that the total monomer conversions 96% and disappearance of 2-(N-hexamethylene-imino)-methyl 1,3-butadiene monomer. One ml of neat ethanol was added to shortstop the polymerization. The polymer cement was then removed from the reactor and stabilized with 1 phm of antioxidant. After evaporating hexanes, the resulting polymer was dried in a vacuum oven at 50° C.

The HTSBR produced was determined to have a glass transition temperature (Tg) at −83° C. and a melting temperature, Tm at 17° C. It was then determined to have a microstructure which contained 3.5 percent 1,2-polybutadiene units, 14.4 percent cis-1,4-polybutadiene units 74.5% trans-1,4-polybutadiene units and 7.6% polystyrene. Both NMR and GPEC indicated the presence of HMI functional groups.

The Mooney viscosity (ML-4) at 100° C. for this polymer was determined to be 98. The GPC measurements indicated that the polymer has a number average molecular weight (Mn) of 107,5000 and a weight average molecular weight (Mw) of 187,30,000. The polydispersity (Mw/Mn) of the resulting polymer is 1.74.

EXAMPLES 23–24

In these examples, high trans polybutadiene and SBR containing 1.0 weight percent of pyrrolidine functional groups were prepared by using 4-(N-pyrrolidinomethyl) styrene as a comonomer. The procedures described in Example 22 were used in these examples except that 1,3-butadiene was used as the main monomer in Example 23. And, 4-(N-pyrrolidinomethyl)styrene was used instead of 2-(N-hexamethylene-imino)-methyl 1,3-butadiene. The polymerization was conducted at 70° C. for 4 hours. The polymer characterization data of these polymers are listed in Table 3.

TABLE 3

| Example No | Polymer | % pyrrolidine | Tg (° C.) | Tm (° C.) | GPC Mn | Mw | Mw/Mn |
|---|---|---|---|---|---|---|---|
| 23 | HTPBD | 1.0 | −90 | 35, 45, 59 | 83,400 | 100,500 | 1.21 |
| 24 | HTSBR | 1.0 | −84 | 27, 39 | 69,540 | 81,300 | 1.17 |

EXAMPLE 25

In this example, a cis-1,4-polybutadiene containing 0.5 weight percent of 2-(N-hexamethyleneimino)-methyl 1,3-butadiene was prepared in a bottle using a catalyst consisting of neodymium neodecanoate/tri-n-octylaluminum/t-butylchloride, at a 1/10/2 molar ratio, at 70° C. for 1 hours. GC analysis of residual monomer showed the polymerization was completed. 2-(N-hexamethyleneimino)-methyl 1,3-butadiene also was consumed. The polybutadiene produced was determined to have a glass transition temperature (Tg) at −111° C. and a melting peak at −6° C. It was also determined to have a microstructure which contained 0.7 percent 1,2-polybutadiene units, 99.3 percent 1,4-polybutadiene units. The polymer was also determined to have a Mn of 324,000 and a Mw of 815,000. The polydispersity (Mw/Mn) was 2.51. The presence of HMI functional groups was also verified by GPEC method.

EXAMPLE 26

In this example, a cis-1,4-polyisoprene containing 0.5 weight percent of 2-(N-hexamethyleneimino)-methyl 1,3-butadiene was prepared in a bottle using a catalyst consisting of neodymium neodecanoate/tri-n-octylaluminum/t-butylchloride, at a 1/10/2 molar ratio, at 70° C. for 2 hours. GC analysis of residual monomer showed the polymerization was completed. 2-(N-hexamethyleneimino)-methyl 1,3-butadiene also was consumed. The polyisoprene produced was determined to have a glass transition temperature (Tg)

at −67° C. The polymer was also determined to have a Mn of 497,000 and a Mw of 1,207,000. The polydispersity (Mw/Mn) was 2.42. The presence of HMI functional groups was also verified by NMR and GPEC techniques.

COMPARATIVE EXAMPLE 27

One mole of neat piperidine was added under nitrogen to a round bottom flask containing. 500 ml of 20–35% aqueous sodium hydroxide. The round bottom flask was equipped with a mechanical stirrer. The mixture was then cooled to 40° F. and one mole of 4-vinyl benzyl chloride or a mixture of 3-vinyl benzyl chloride and 4-vinyl benzyl chloride was added drop-by-drop to the mixture for a period of 30–60 minutes at a temperature of 40° F. to 50° F. Upon completion of the addition, the reaction mixture was heated to room temperature with the stirring being continued for a period of 2 to 4 hours. The reaction mixture was then extracted with toluene or diethyl ether. The organic filtrate was then dried over potassium hydroxide (KOH) pellets.

The toluene or diethyl ether was then removed from the dried filtrate using a rotary evaporator under reduced pressure. The neat pyrrolidinomethyl styrene was then recovered by vacuum distillation. The boiling points of the mixture of 3-N-piperidinomethyl styrene and 4-N-piperidinomethyl styrene was 115–120° C. at 0.5 mm-Hg. The yield was about 70 percent.

By utilizing a similar procedure 4-N-hexamethylene iminomethyl styrene, 4-N-pyrrolidino methyl styrene, and 4-N-dialkyl amino styrene or mixtures of 3-isomers and 4-isomers can be prepared.

COMPARATIVE EXAMPLES 28–32

In this series of experiments the rubber samples made in Examples 6–10 were compounded with 55 phr (parts by weight per 100 parts by weight of rubber) of carbon black and cured. The physical properties of the compounded rubber samples are shown Table 4.

TABLE 4

| Example | Rubber from Example No. | Percent Functionalized Monomer | Uncured G' (15% @ 0.83 Hz) | Cured G' (5% @ 1 Hz) | Cured tan delta (5% @ 1 Hz) |
|---|---|---|---|---|---|
| 28 | 10 | 0.0 | 142 kPa | 2.0 MPa | 0.178 |
| 29 | 7 | 0.25 | 192 kPa | 1.6 MPa | 0.113 |
| 30 | 8 | 0.50 | 242 kPa | 1.8 MPa | 0.122 |
| 31 | 6 | 1.0 | 281 kPa | 1.5 MPa | 0.119 |
| 32 | 9 | 0.5* | 405 kPa | 1.6 MPa | 0.097 |

*The rubber was also coupled with tin tetrachloride (SnCl$_4$).

This series of experiments shows that the solution elastomer compositions with functionalized monomers exhibited increased uncured viscosity (G' at 15% strain) indicating the presence of strong interactions between polymer and filler. The composition with functional comonomer also showed significantly reduced tan delta values indicating that improved rolling resistance would be realized if the rubber was used in tire tread compounds.

EXAMPLE 33

In this experiment 3-(2-Pyrrolidinoethyl) and 4-(2-Pyrrolidinoethyl) styrene were syntnesized. In the procedure used 1030 g of 80% Divinylbenzene (824 g of pure divinylbezene 6.324 moles; the ratio of meta-DVB to para-DVB was normally 60:40) was added under nitrogen to a 5 litter flask equipped with a stirrer that contained 2 liters of dry hexane. To this homogenous solution was added 6.239 moles (450 g or 528 ml of dry prrolidine). This homogenous solution was cooled with Wet/Ice acetone to negative 5 degrees Centigrade. At this temperature 2.5% of the 6329 mmoles which is 155.9 mmoles of n-Butyllithium was added all at once. The reaction temperatures rose to +55° C. The reaction was allowed to cool down to +5° C. for one hr. After that the reaction was neutralized with distilled water, three samples were taken for GC analysis. Sample 1 is taken when all the ingredients are added except the catalyst, n-Butyllithium. Sample 2 was taken after the n-Butyllithium is added. Sample 3 was taken after the water was added. The GC analysis of the Samples is provided in FIGS. 1–3.

Gas Chromatography (GC) was used to monitor the conversion of the divinylbenzene (DVB) and pyrrolidine into the 1-pyrrolidino ethyl styrene (PES) monomer. FIG. 1 (Sample 1) shows the initial charge of DVB and pyrrolidine in the reactor. In FIG. 1, the elution times and relative amounts of materials are shown. For example, hexane has an elution time of 5.7 minutes and a normalized amount of 56.32%. Ethylbenzene and DVB are as follows: 11.36 and 11.44 minutes are both ethylbenzene peaks, whereas at 11.61 and 11.72 minutes the meta- and para-DVB peaks are seen. From the data, 34.6% of the mixture appears to be DVB.

TABLE 1

Gas Chromatograph of initial charge of DVB and pyrrolidine into the reactor (Sample 1)
AREA %

| RT | AREA | TYPE | WIDTH | AREA % |
|---|---|---|---|---|
| 4.595 | 339 | BP | .007 | .00932 |
| 4.701 | 1084 | PB | .022 | .02981 |
| 5.700 | 2048127 | ++ | .029 | 56.32285 |
| 11.360 | 164258 | BV | .041 | 4.51704 |
| 11.439 | 136359 | VB | .040 | 3.74983 |

TABLE 1-continued

Gas Chromatograph of initial charge of DVB and pyrrolidine into the reactor (Sample 1)
AREA %

| RT | AREA | TYPE | WIDTH | AREA % |
|---|---|---|---|---|
| 11.612 | 861395 | PV | .049 | 23.68809 |
| 11.715 | 380831 | VB | .043 | 10.47273 |
| 12.192 | 2161 | PB | .062 | .05943 |
| 16.025 | 41852 | BB | .190 | 1.15092 |

TOTAL AREA = 3636406
MUL FACTOR = 1.0000E+00

Table 2 (Sample 2) monitors the reaction conversion just after the addition of n-butyllithium (n-BuLi). In this chromatograph, the elution times are very similar to those in FIG. 1: 5.7 minutes—hexane, 11.36 and 11.44 minutes—ethylbenzene, 11.60 and 11.69 minutes—meta- and para-DVB, and the meta- and para-PES (product) is eluded at 17.35 and 17.79 minutes. As shown here, the reaction is quite fast. The amount of DVB left is roughly 9.26%, which means 73% conversion based upon the DVB.

TABLE 2

Gas Chromatograph after the addition of n-BuLi (Sample 2) AREA %

| RT | AREA | TYPE | WIDTH | AREA % |
|---|---|---|---|---|
| 4.702 | 894 | PB | .019 | .02446 |
| 5.700 | 1740519 | ++ | .029 | 47.62819 |
| 11.360 | 132588 | BV | .040 | 3.62819 |
| 11.438 | 122925 | VB | .040 | 3.36376 |
| 11.595 | 282819 | BV | .043 | 7.73916 |
| 11.691 | 31833 | VB | .041 | .87109 |
| 12.192 | 2221 | PB | .064 | .06078 |
| 16.024 | 198043 | BB | .258 | 5.41932 |
| 16.610 | 39871 | BB | .055 | 1.09104 |
| 16.954 | 14928 | PB | .057 | .40850 |
| 17.348 | 660404 | PB | .074 | 18.07154 |
| 17.790 | 427343 | PB | .070 | 11.69397 |

TOTAL AREA = 3654389
MUL FACTOR = 1.0000E+00

Table 3 (Sample 3) is the gas chromatograph of the reaction one hour after the addition of the n-BuLi. Once again the elution times are nearly identical to those seen in FIG. 2. Here the DVB amounts to 6.87%, which corresponds to nearly 80% conversion based on DVB.

TABLE 3

Gas chromatograph after one hour of reaction time (Sample 3) AREA %

| RT | AREA | TYPE | WIDTH | AREA % |
|---|---|---|---|---|
| 4.595 | 156 | BP | .003 | .00438 |
| 4.702 | 875 | PB | .018 | .02455 |
| 5.700 | 1802240 | ++ | .029 | 50.56275 |
| 11.360 | 130641 | BV | .040 | 3.66520 |
| 11.438 | 125575 | VB | .040 | 3.52307 |
| 11.593 | 220571 | BV | .042 | 6.18823 |
| 11.690 | 18478 | VB | .041 | .51841 |
| 12.192 | 2444 | PB | .067 | .06857 |
| 14.335 | 9175 | BB | .226 | .25741 |
| 16.611 | 53265 | BB | .054 | 1.49438 |
| 16.955 | 20423 | BB | .057 | .57298 |
| 17.355 | 729062 | PB | .075 | 20.45419 |
| 17.796 | 451459 | PB | .071 | 12.66591 |

TOTAL AREA = 3564365
MUL FACTOR = 1.0000E+00

After drying the reaction mixture with magnesium sulfate, the hexane in the filtrate was evaporated and the resulting residue was distilled at reduced pressure to yield a mixture of 3 and 4-(2-pyrrolidinoethyl)styrene.

The boiling point was 105–110° C. at 0.3 mm-Hg. The product contains 96% of a mixture of 3-(2-pyrrolidinoethyl) styrene and 4-(2-pyrrolidinoethyl) styrene and 4% of a mixture of 3-(2-pyrrolidinoethyl) styrene and 4-(2-pyrrolidinoethyl)-1-ethylbenzene as determined by proton NMR in $CDCl_3$. The ratio of 3-(2-pyrrolidinoethyl)styrene to 4-(2-pyrrolidinoethyl)styrene was normally 60:40.

EXAMPLE 34

In this experiment, a 2/18/80 pyrrolidinoethylstyrene/styrene/1,3-butadiene terpolymer was prepared. In the procedure used, 2068 grams of a silica/alumina/molecular sieve dried premix containing 20.14 weight percent of pyrrolidinoethyl styrene, styrene and 1,3-butadiene in hexane was charged into a one-gallon (3.8 liters) reactor. The pyrrolidinoethylstyrene (PES) used contained a mixture of 3-(2-pyrrolidinoethyl) styrene and 4-(2-pyrrolidinoethyl) styrene and a small amount of mixed 3-(2-pyrrolidinoethyl)-1-ethylbenzene and 4-(2-pyrrolidinoethyl)-1-ethylbenzene. The ratio of 3-(2-pyrrolidinoethyl) styrene to 4-(2-pyrrolidinoethyl)styrene could be varied, although it was normally 60:40. The ratio of PES to styrene to 1,3-butadiene ratio was 2:18:80. Then, 0.48 ml of neat N,N,N',N'-tetramethylethylenediamine (TMEDA) and 1.5 ml of 1.6 M n-butyl lithium (n-BuLi) in hexanes solvent were added to the reactor. The molar ratio of TMEDA to n-BuLi was 1.5:1. The polymerization was carried out at a temperature of 70° C. for 90 minutes. A GC analysis of the residual monomer contained in the polymerization mixture indicated that the all monomers had been consumed by this time. The polymer cement was then shortstopped with ethanol and removed from the reactor and stabilized with 1 phm of antioxidant. After evaporating hexane, the resulting polymer was dried in a vacuum oven at 50° C. The GC analysis of the residual monomer with respect to the polymerization time also indicated that PES was randomly distributed along the polymer chain.

The PES-styrene-butadiene terpolymer produced was determined to have a glass transition temperature (Tg) at −34° C. It was also determined to have a microstructure which contained 48.0 percent 1,2-polybutadiene units, 32.9 percent 1,4-polybutadiene units, 17.4 percent random polystyrene units and 1.7 percent of PES units. The Mooney viscosity (ML-4) at 100° C. for this polymer was determined to be 42. The GPC data of this polymer was also determined to have a number average molecular weight (Mn) of 181,900 and weight average molecular weight (Mw) of 190,700. The polydispersity (Mw/Mn) of the polymer was 1.05.

Other PES-styrene-butadiene terpolymers containing 0.25, 0.5, 1.0 and 5.0 weight percent PES having similar glass transition temperatures within the range of −32° C. to −37° C. were prepared similarly for compound evaluation.

COMPARATIVE EXAMPLE 35

In this example, a 2/18/80 pyrrolidinomethylstyrene/styrene/1,3-butadiene terpolymer was prepared using the procedures described in Example 34 except that pyrrolidinomethyl styrene (PMS) was used instead of PES. The PMS was prepared from vinylbenzylchloride and normally was a mixture 3-pyrrolidino methyl) styrene and 4-(pyrrolidino methyl) styrene. The molar ratio of 3-(pyrrolidinomethyl) styrene to 4-(pyrrolidino methyl) styrene was normally closed to 60:40. Also, 0.55 ml of a neat TMEDA and 2.1 ml of 1.6 M n-BuLi were used as the initiator.

The PMS-styrene-butadiene terpolymer produced was determined to have a glass transition temperature (Tg) at −34° C. The Mooney viscosity (ML-4) at 100° C. for this polymer was determined to be 37. The GPC data of this polymer was also determined to have a Mn of 147,100 and Mw of 180,600. The polydispersity (Mw/Mn) was 1.23. The polydispersity of this polymer is significantly higher than that of PES-styrene-butadiene terpolymer obtained in Example 1 (1,23 vs. 1.05), indicating side reactions might occur when PMS was used as a co-monomer.

EXAMPLE 36

In this experiment, a tin coupled 1/19/80 pyrrolidinoethylstyrene/styrene/1,3-butadiene terpolymer was prepared. A total of 2006 grams of a silica/alumina/molecular sieve dried premix containing 20.4 weight percent of pyrrolidinoethyl styrene (PES), styrene and 1,3-butadiene in hexane was charged into a one-gallon (3.8 liters) reactor. The PES to styrene to 1,3-butadiene ratio was 1:19:80. Then, 0.52 ml of neat N,N,N',N'-tetramethylethylenediamine (TMEDA) and 2.0 ml of 1.6 M n-butyl lithium (n-BuLi) in hexane were added to the reactor, respectively. The polymerization was carried out at 70° C. for 90 minutes. The GC analysis of the residual monomer contained in the polymerization mixture indicated that all of the monomer had been consumed by that time. Then, 250 grams of the polymer cement was removed from the reactor and stabilized with 1 phm of antioxidant. Then, 1.30 ml of a 1 M tin tetrachloride solution in hexane was added to the remaining cement in the reactor. The molar ratio of tin tetrachloride to n-BuLi was 0.5:1. The coupling reaction was conducted at 70° C. for 30 minutes. The polymer cement was then removed from the reactor and stabilized with 1 phm of antioxidant. After evaporating the hexane solvent, the resulting polymer was dried in a vacuum oven at 50° C.

The PES-styrene-butadiene terpolymer produced was determined to have a glass transition temperature (Tg) at −35° C. The Mooney viscosity (ML-4) at 100° C. for this polymer was determined to be 81. The Mooney ML-4 viscosity of the base polymer was also determined to be 16. The GPC data indicated that the coupling efficiency was 75%.

EXAMPLES 37–40

In these examples, tin coupled PES-styrene-butadiene terpolymers containing 0.25, 0.5, 2.0 and 5.0% PES were prepared using the procedures described in Example 3 except that the amount of PES was changed from 1.0% to 0.25, 0.5, 2.0 and 5,0%. The molar ratio of tin tetrachloride to n-BuLi was kept the same (0.5:1). The Tg, Mooney viscosity and the percent coupling of these polymers are listed in Table 5.

TABLE 5

| Example | % PES | Tg (° C.) | ML-4 Base | ML-4 Coupled | % Coupling |
|---|---|---|---|---|---|
| 37 | 0.25 | −36 | 25 | 106 | 80 |
| 38 | 0.50 | −39 | 19 | 95 | 77 |
| 36 | 1.00 | −35 | 16 | 81 | 75 |
| 39 | 2.00 | −35 | 17 | 65 | — |
| 40 | 5.00 | −37 | 16 | 81 | — |

EXAMPLE 41

In this example, a silicone coupled PES-styrene-butadiene terpolymer containing 2.0% PES was prepared using the procedures described in Example 36 except that the amount of PES was changed from 1.0% to 2.0% and silicon tetrachloride was used as the coupling agent. The molar ratio of silicon tetrachloride to n-BuLi was kept the same (0.5:1). The polymer was determined to have a glass transition temperature (Tg) at −36° C. The Mooney viscosity of base and silicon coupled polymers were 17 and 86, respectively.

EXAMPLES 42–43

In these examples, coupled PES-styrene-butadiene terpolymers containing 1.0% PES were prepared using the procedures described in Example 36 except that the silicon tetrachloride, and a mixture containing 50% tin tetrachloride and 50% silicon tetrachloride were used as coupling agents The molar ratio of coupling agent to n-BuLi was kept the same (0.5:1). The glass transition temperature (Tg), Mooney viscosity, and the percent of coupling agent used are listed in Table 6.

TABLE 6

| Example | % PES | Coupling agent | Tg (° C.) | ML-4 Base | ML-4 Coupled | % Coupling |
|---|---|---|---|---|---|---|
| 42 | 1.00 | SiCl4 | −32 | 21 | 97 | 81 |
| 43 | 1.00 | 50/50 SiCl4/SnCl4 | −33 | 21 | 89 | 75 |

EXAMPLES 44–45

In these examples, tin coupled PES-styrene-butadiene terpolymers containing 1.0% PES were prepared using the procedures described in Example 36 except that the molar ratio of tin tetrachloride to n-BuLi was changed from 0.5:1 to 0.25:1 and 0.375:1, respectively. The Tg, Mooney viscosity and the percent coupling of these polymers are listed in Table 7.

TABLE 7

| Example | % PES | SnCl4/n-BuLi ratio | Tg (° C.) | ML-4 Base | ML-4 Coupled | % Coupling |
|---|---|---|---|---|---|---|
| 44 | 1.00 | 0.25:1 | −36 | 13 | 81 | 81 |
| 45 | 1.00 | 0.375:1 | −37 | 12 | 77 | 77 |
| 36 | 1.00 | 0.50:1 | −35 | 16 | 81 | 75 |

COMPARATIVE EXAMPLES 46

In this example, tin coupled PMS-styrene-butadiene terpolymer containing 1.0% PMS was prepared using the procedures described in Example 36 except that the molar ratio of tin tetrachloride to n-BuLi was changed from 0.5:1 to 0.25:1. The Tg, Mooney viscosity and the percent coupling of this polymer are listed in Table 8. As shown in Table 8, a PES functionalized polymer can be more effectively coupled with tin tetrachloride than the PMS functionalized polymer. Polymers with better tin coupling normally provide better compound properties.

TABLE 8

| Example | % Functional monomer | SnCl$_4$/n-BuLi ratio | Tg (° C.) | ML-4 Base | ML-4 Coupled | % Coupling |
|---|---|---|---|---|---|---|
| 46 | 1% PMS | 0.25:1 | −33 | 18 | 65 | 62 |
| 44 | 1% PES | 0.25:1 | −36 | 13 | 81 | 81 |

EXAMPLE 47

In this example, a 1/11/88 PES/styrene/1,3-butadiene terpolymer was prepared using the procedure described in Example 34 except that the ratio of PES to styrene and to 1,3-butadiene was changed to 1:11:80 and the molar ratio of TMEDA to n-BuLi was also changed to 1:1. GC analysis of residual monomer with respect to polymerization time indicated that PES was randomly distributed along the polymer chain. The resulting terpolymer had a Tg at −42° C. and was determined to a have a ML-4 of 47.

EXAMPLE 48

In this example, a 1/99 PES/isoprene copolymer was prepared using the procedure described in Example 34 except that a mixture of PES and isoprene in hexane was used as the monomer premix and DTP (2,2-di-tetrahydrofuryl propane) was used as the modifier. The molar ratio of DTP to n-BuLi was 2.5:1. GC analysis of residual monomer indicated that the polymerization was completed in an hour. The resulting copolymer had a Tg at −14° C. and was determined to a have a ML-4 of 82.

EXAMPLES 49–65

In this series of experiments tire tread compounds that were loaded with carbon black as a filler were make with styrene-butadiene rubber that had various amounts of a mixture of 3-(2-pyrrolidinomethyl)styrene and 4-(2-pyrrolidinomethyl)styrene (PMS) incorporated therein. The amount of functionalized styrene monomer that was incorporated into the styrene-butadiene rubber is shown in Table 9. These tire tread compositions were made by mixing 55 phr (parts by weight per 100 parts by weight of rubber) of N299 carbon black, 10 phr of processing oil, 3 phr of zinc oxide, 2 phr of stearic acid, 1.5 phr of antioxidant, 1.2 phr of sulfenamide accelerator, and 1.4 phr of sulfur into various styrene-butadiene rubbers having different contents of bound functionalized styrene monomer. The characterization of the tire tread compounds made are shown in Table 9 (G' was measure on uncured compounds and tan delta was measured on cured samples at 60° C.).

TABLE 9

| Example | PMS | Macrostructure | ML-4* | G' (kPa) | Tan delta |
|---|---|---|---|---|---|
| 49 | 0% | linear | 41 | 500 | 0.177 |
| 50 | 0% | linear | 63 | 595 | 0.170 |
| 51 | 0.25% | linear | 65 | 584 | 0.149 |
| 52 | 0.25% | linear | 66 | 606 | 0.135 |
| 53 | 0.5% | linear | 27 | 499 | 0.165 |
| 54 | 0.5% | linear | 27 | 500 | 0.145 |
| 55 | 0.5% | linear | 32 | 520 | 0.146 |
| 56 | 0.5% | linear | 60 | 614 | 0.124 |
| 57 | 0.5% | tin coupled | 77 | 549 | 0.105 |
| 58 | 1% | linear | 47 | 612 | 0.116 |
| 59 | 1% | linear | 62 | 645 | 0.106 |
| 60 | 1% | tin coupled | 68 | 504 | 0.108 |
| 61 | 2% | linear | 25 | 393 | 0.160 |
| 62 | 2% | linear | 36 | 466 | 0.135 |
| 63 | 2% | linear | 65 | 554 | 0.124 |
| 64 | 5% | linear | 46 | 540 | 0.115 |
| 65 | 10% | linear | 44 | 581 | 0.107 |

*Mooney ML 1 + 4 viscosity

It is desirable for tan delta to be as low as possible at 60° C. because the hysteresis of rubber is lower at lower tan delta values. Accordingly, tire tread compound that have lower tan delta values will have less heat build-up and lower rolling resistance. As can be seen from Table 9, the incorporation of the PMS into the styrene-butadiene rubber caused a reduction in tan delta at 60° C. The incorporation of 0.25 weight percent of PMS into the styrene-butadiene rubber caused a significant reduction in tan delta. The incorporation of higher level of bound PMS into the styrene-butadiene rubber caused greater reduction in tan delta values.

EXAMPLES 66–86

In this series of experiments tire tread compounds were make with styrene-butadiene rubber that had various amounts of a mixture of 3-(2-pyrrolidinoethyl)styrene and 4-(2-pyrrolidinoethyl)styrene (PES) incorporated therein. The amount of functionalized styrene monomer that was incorporated into the styrene-butadiene rubber is shown in Table 10. These tire tread compositions were made as described in Examples 49–65. The characterization of the tire tread compounds made are shown in Table 10 (G' was measure on uncured compounds and tan delta was measured on cured samples at 60° C.).

TABLE 10

| Example | PES | Macrostructure | ML-4* | G' (kPa) | Tan delta |
|---|---|---|---|---|---|
| 66 | 0% | linear | 41 | 500 | 0.177 |
| 67 | 0% | linear | 63 | 594 | 0.170 |
| 68 | 0.25% | linear | 25 | 556 | 0.127 |
| 69 | 0.25% | linear | 32 | 597 | 0.114 |
| 70 | 0.25% | linear | 49 | 610 | 0.107 |
| 71 | 0.25% | tin coupled | 106 | 612 | 0.104 |
| 72 | 0.5% | linear | 19 | 590 | 0.119 |
| 73 | 0.5% | linear | 30 | 609 | 0.110 |
| 74 | 0.5% | linear | 49 | 608 | 0.088 |
| 75 | 0.5% | tin coupled | 95 | 627 | 0.094 |
| 76 | 1% | linear | 16 | 510 | 0.122 |
| 77 | 1% | linear | 42 | 620 | 0.105 |
| 78 | 1% | tin coupled | 81 | 570 | 0.091 |
| 79 | 2% | linear | 17 | 517 | 0.110 |
| 80 | 2% | linear | 42 | 619 | 0.096 |
| 81 | 2% | linear | 60 | 619 | 0.085 |
| 82 | 2% | tin coupled | 65 | 572 | 0.091 |
| 83 | 5% | linear | 25 | 605 | 0.091 |
| 84 | 5% | tin coupled | 47 | 554 | 0.101 |
| 85 | 5% | linear | 48 | 628 | 0.084 |
| 86 | 5% | tin coupled | 64 | 672 | 0.080 |

*Mooney ML 1 + 4 viscosity

As has been explained it is desirable for the tan delta of tire tread compounds to be as low as possible. As can be seen from Table 10, the incorporation of the PES into the styrene-butadiene rubber caused a reduction in tan delta at 60° C. As can been seen by comparing Table 10 to Table 9, the incorporation of PES into the styrene-butadiene rubber caused a greater reduction in tan delta than did the incorporation of PMS into the styrene-butadiene rubber.

EXAMPLES 87–91

In this series of experiments tire tread compounds that were loaded with silica as a filler were make with styrene-butadiene rubber that had various amounts of a mixture of 3-(2-pyrrolidinomethyl)styrene and 4-(2-pyrrolidinomethyl) styrene (PMS) incorporated therein. The amount of functionalized styrene monomer that was incorporated into the styrene-butadiene rubber is shown in Table 11. These tire tread compositions were made by mixing 55 phr of silica, 10 phr of processing oil, 3 phr of zinc oxide, 2 phr of stearic acid, 1.5 phr of antioxidant, 1.5 phr of sulfenamide accelerator, and 1.4 phr of sulfur into styrene-butadiene rubbers-having different contents of bound functionalized styrene monomer. The characterization of the tire tread compounds made are shown in Table 11 (G' was measure on uncured compounds and tan delta was measured on cured samples at 60° C.).

TABLE 11

| Example | PMS | ML-4* | G' (kPa) | Tan delta |
|---|---|---|---|---|
| 87 | 0% | 41 | 890 | 0.235 |
| 88 | 1% | 47 | 800 | 0.157 |
| 89 | 5% | 46 | 596 | 0.098 |
| 90 | 10% | 44 | 674 | 0.086 |
| 91 | 20% | 47 | 441 | 0.088 |

*Mooney ML 1 + 4 viscosity

As has been explained it is desirable for the tan delta of tire tread compounds to be as low as possible. As can be seen from Table 11, the incorporation of the PMS into the styrene-butadiene rubber caused a reduction in tan delta at 60° C. Higher levels of PMS caused greater reductions in tan delta. This series of experiments also that it is possible to eliminate silica coupling agent from tire tread compounds that are made utilizing styrene-butadiene rubbers that contain a small amount of bound PMS.

EXAMPLES 92–96

In this series of experiments tire tread compounds that were loaded with silica as a filler were make with styrene-butadiene rubber that had various amounts of a mixture of 3-(2-pyrrolidinomethyl)styrene and 4-(2-pyrrolidinomethyl) styrene (PMS) incorporated therein. The amount of functionalized styrene monomer that was incorporated into the styrene-butadiene rubber is shown in Table 11. These tire tread compositions were made by mixing 55 phr of silica, 10-phr of processing oil, 3 phr of zinc oxide, 2 phr of stearic acid, 1.5 phr of antioxidant, 1.5 phr of sulfenamide accelerator, 1.4 phr of sulfur, and 4.4 phr of silica coupling agent into styrene-butadiene rubbers having different contents of bound functionalized styrene monomer. The characterization of the tire tread compounds made are shown in Table 12 (G' was measure on uncured compounds and tan delta was measured on cured samples at 60° C.).

TABLE 12

| Example | PMS | ML-4* | G' (kPa) | Tan delta |
|---------|-----|-------|----------|-----------|
| 92 | 0% | 41 | 754 | 0.173 |
| 93 | 1% | 47 | 720 | 0.132 |
| 94 | 5% | 46 | 647 | 0.098 |
| 95 | 10% | 44 | 617 | 0.081 |
| 96 | 20% | 47 | 474 | 0.087 |

*Mooney ML 1 + 4 viscosity

As has been explained it is desirable for the tan delta of tire tread compounds to be as low as possible. As can be seen from Table 12, the incorporation of the PMS into the styrene-butadiene rubber caused a reduction in tan delta at 60° C. Higher levels of PMS caused greater reductions in tan delta. This series of experiments also that it is possible to reduce the level of silica coupling agent in tire tread compounds that are made utilizing styrene-butadiene rubbers that contain a small amount of bound PMS and still realize good results.

EXAMPLES 97–102

In this series of experiments tire tread compounds that were loaded with silica as a filler were make with styrene-butadiene rubber that had-various amounts of a mixture of 3-(2-pyrrolidinoethyl)styrene and 4-(2-pyrrolidinoethyl) styrene (PES) incorporated therein. The amount of functionalized styrene monomer that was incorporated into the styrene-butadiene rubber is shown in Table 13. These tire tread compositions were made by mixing 78 phr of silica, 28 phr of processing oil, 2.5 phr of zinc oxide, 2 phr of stearic acid, 3 phr of antioxidant, 3 phr of siland coupler, 1.6 phr of sulfenamide accelerator, 1.9 phr of guanadiene accelerator, and 2.1 phr of sulfur into styrene-butadiene rubbers having different contents of bound functionalized styrene monomer. The characterization of the tire tread compounds made are shown in Table 13 (G' was measure on uncured compounds and tan delta was measured on cured samples at 60° C.).

TABLE 13

| Example | PMS | ML-4* | G' (kPa) | Tan delta |
|---------|-----|-------|----------|-----------|
| 97 | 0% | 41 | 465 | 0.145 |
| 98 | 0.25% | 49 | 645 | 0.151 |
| 99 | 0.5% | 49 | 681 | 0.141 |
| 100 | 1% | 42 | 657 | 0.120 |
| 101 | 2% | 42 | 749 | 0.102 |
| 102 | 5% | 48 | 869 | 0.073 |

*Mooney ML 1 + 4 viscosity

As can be seen from Table 13, the incorporation of the PES into the styrene-butadiene rubber caused a reduction in tan delta at 60° C. Higher levels of PMS caused greater reductions in tan delta. This series of experiments also that it is possible to reduce the level of silica coupling agent in tire tread compounds that are made utilizing styrene-butadiene rubbers that contain a small amount of bound PES and still realize good results.

By utilizing styrene-butadiene rubber that has been modified by incorporation a small amount of PES therein tire tread compounds can be made that exhibit lower hysteresis and that can be processed more easily. Silica loaded tire tread compounds can also be made with significantly lower levels of silica coupling agent. This is an extremely important benefit since silica coupling agents are expensive relative to most other materials used in tire tread compounds. The amount of silica coupling agent needed in such compounds can typically be reduced to a level within the range of 0 phs (parts by weight per 100 parts by weight of silica) to 5 phs. More typically the level of silica coupling agent is reduced to be within the range of 1 phs to 4 phs. The level of silica coupling agent is most typically reduced to a level within the range of 1 phs to 2 phs.

Functionalized styrene monomers which are of the structural formula:

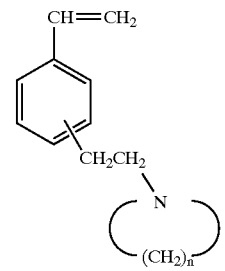

wherein n represents an integer from 4 to about 10 are some of the most beneficial functionalized styrene monomers that can be utilized in the practice of this invention. In such functionalized styrene monomers it is preferred form n to represent 4 or 6. PES (wherein n represents 4) is the most preferred.

While certain representative embodiments and details have been shown for the purpose of illustrating the subject invention, it will be apparent to those skilled in this art that various changes and modifications can be made therein without departing from the scope of the subject invention.

EXAMPLES 103–105

Linear Polymerization of 1% PES/19% Styrene/80% Butadiene

Premix Preparation 101.4 g of 93% PES in hexane was added to a 20.27% butadiene in hexane premix cylinder via syringe under inert atmosphere to yield a solution with a monomer weight percent ratio of 98.73% 1,3-butadiene and 1.27% PES. The cylinder contained 7,298.6 g 1,3-Butadiene, 94.3 g PES and 28,607.1 g hexane. The cylinder contents were mixed using a high shear mixer. Note that the PES can be added to either butadiene or styrene in this manner. A styrene premix cylinder containing 36,000 g of 20.98% styrene in hexane was then prepared.

Polymerization

The desired product was linear 1PES/19Styrene/80Butadiene SSBR copolymer with a Mooney viscosity of 75 and a Tg midpoint of −35° C. made continuously. Although the desired product specifies 1% PES, this copolymer can be synthesized with a range of 0.25%–2% PES. To meet these desired product specifications the polymerization was performed under the following operating conditions:

- Monomer weight percent ratio into first reactor of 1PES/19Styrene/80Butadiene
- 0.6897 mmoles n-butyllithium per 100 g monomer (Target Mn of 145,000)
- 75 parts 1,2-butadiene per million parts monomer
- 2.0 mmoles TMEDA per mole n-butyllithium
- Reactor 1 Temp of 194° F.
- Reactor 2 Temp of 190° F.
- Total retention time of 1 hour The continuous unit contains two one gallon CSTR's in series equipped with mechanical agitators under inert atmosphere, followed by a five gallon cement holding tank. Styrene, 1,3-butadiene and PES, 1,2-butadiene, and TMEDA were brought together and then were added to the first reactor where they met the n-butyllithium. After achieving steady state, percent solids were used to monitor total monomer conversion, whereas GC analysis provided individual monomer consumption. GC results can be seen in Table 14.

The product was collected in a cement tank where it was terminated with 1 mole isopropanol per mole n-BuLi (shortstop) and 1 part per hundred monomer of Paratax (antioxidant). Polymer was air dried in a 130° F. oven for three days. Testing of the dry raw polymer includes Mooney Large, DSC, GPC and NMR. Results from these tests can be seen in Tables 15 and 16.

TABLE 14

Monomer Conversion via Gas Chromatograph
Total % Monomer Conversion

| % Butadiene | % Styrene | % Functional Mon. | % Total Conv. |
|---|---|---|---|
| 97.95 | 96.36 | 99.88 | 97.67 |

TABLE 15

Linear Polymer Characterizations

| | DSC (° C.) | | | GPC Analysis | | | |
|---|---|---|---|---|---|---|---|
| ML + 4 | Onset Tg | Inflection Tg | End Tg | Mn | Mw | Mz | Mw/Mn |
| 74 | −42.02 | −39.32 | −36.67 | 179,500 | 335,500 | 640,200 | 1.87 |

TABLE 16

NMR Data for Linear Polymer

| Trans 1,4- BD | Cis 1,4- BD | 1,2- BD | DVCH | Styrene | Styrene Sequence | | | PyrES |
|---|---|---|---|---|---|---|---|---|
| | | | | | 1S | 2-4S | >/=5S | |
| 24.7 | 15.6 | 35.7 | 5.0 | 17.8 | 16.4 | 1.3 | 0.1 | 1.2 |

Coupled Polymerization of 1% PES/19% Styrene/80% Butadiene

The procedures outlined above were also used for coupled polymerizations with tin tetrachloride, silicon tetrachloride, and a combination of the two. There are only slight variations in the operating conditions. The coupling agent was added in a ratio of 0.25 moles coupling agent per mole n-butyllithium.

The desired product was coupled 1PES/19Styrene/80Butadiene SSBR copolymer with a linear base Mooney viscosity of 35, a coupled Mooney viscosity of 90 and a Tg midpoint of −35° C. made continuously. To meet these specifications the polymerization was performed under the following operating conditions:

- Monomer weight percent ratio into first reactor of 1PES/19Styrene/80Butadiene
- 0.8091 mmoles n-butyllithium per 100 g monomer (Target Mn of 120,000)
- 75 parts 1,2-butadiene per million parts monomer
- 2.0 mmoles TMEDA per mole n-butyllithium
- 0.25 moles 2% coupling agent (both SnCl$_4$ and SiCl$_4$) in hexane per mole n-butyllithium
- Reactor 1 Temp of 194° F.
- Reactor 2 Temp of 190° F.
- Total retention time of 1 hour The coupling agent is introduced to the polymerization in a high shear cement mixer located after the second reactor and before the cement holding tank. The hold time in the cement mixer is approximately four minutes. Tables 17–19 include characterization data for these copolymers.

TABLE 17

Monomer Conversion via Gas Chromatograph
Total % Monomer Conversion

| % Butadiene | % Styrene | % Functional Mon. | % Total Conv. |
|---|---|---|---|
| 99.03 | 98.65 | 99.88 | 98.97 |

TABLE 18

Linear Polymer Characterizations

| ML + 4 Base SnCl$_4$ SiCl$_4$ | DSC (° C.) | | | GPC Analysis | | | |
|---|---|---|---|---|---|---|---|
| | Onset Tg | Inflection Tg | End Tg | Mn | Mw | Mz | Mw/Mn |
| 42 | −38.5 | −35.8 | −33.0 | 127,000 | 274,800 | 647,800 | 2.16 |
| 88 | −40.1 | −36.7 | −33.3 | 147,900 | 424,100 | 1,471,000 | 2.87 |
| 74 | −39.0 | −36.2 | −33.4 | 148,500 | 392,900 | 1,158,000 | 2.65 |

TABLE 19

NMR Data for Linear Polymer

| Trans 1,4- BD | Cis 1,4- BD | 1,2- BD | DVCH | Styrene | Styrene Sequence | | | |
|---|---|---|---|---|---|---|---|---|
| | | | | | 1S | 2-4S | >/=5S | PyrES |
| 21.3 | 15.3 | 37.4 | 5.0 | 20.1 | 18.3 | 1.4 | 0.5 | 0.9 |

Coupled Polymerization of 0.5% PES/19.5% Styrene/80% Butadiene

Once again, the procedures outlined above were used for coupled polymerizations with tin tetrachloride, silicon tetrachloride. There are only slight variations in the operating conditions. The coupling agent was added in a ratio of 0.25 moles coupling agent per mole n-butyllithium.

The desired product was coupled 0.5PES/19.5Styrene/80Butadiene SSBR copolymer with a linear base Mooney viscosity of 27, a coupled Mooney viscosity of 90 and a Tg midpoint of −35° C. made continuously. To meet these specifications the polymerization was performed under the following operating conditions:

Monomer weight percent ratio into first reactor of 1PES/19Styrene/80Butadiene 0.8091 mmoles n-butyllithium per 100 g monomer (Target Mn of 120,000)

75 parts 1,2-butadiene per million parts monomer 2.0 mmoles TMEDA per mole n-butyllithium 0.25 moles 2% coupling agent (both $SnCl_4$ and $SiCl_4$) in hexane per mole n-butyllithium Reactor 1 Temp of 194° F.

Reactor 2 Temp of 190° F.

Total retention time of 0.5 hours

The coupling agent is introduced to the polymerization in a high shear cement mixer located after the second reactor and before the cement holding tank. The hold time in the cement mixer is approximately four minutes. Tables 20–22 include characterization data for these copolymers.

TABLE 20

Monomer Conversion via Gas Chromatograph
Total % Monomer Conversion

| % Butadiene | % Styrene | % Functional Mon. | % Total Conv. |
|---|---|---|---|
| 98.55 | 96.69 | 99.55 | 98.14 |

TABLE 21

Linear Polymer Characterizations

| ML + 4 Base $SnCl_4$ $SiCl_4$ | DSC (° C.) | | | GPC Analysis | | | |
|---|---|---|---|---|---|---|---|
| | Onset Tg | Inflection Tg | End Tg | Mn | Mw | Mz | Mw/Mn |
| 32 | −37.7 | −35.1 | −32.4 | 120,100 | 189,400 | 276,200 | 1.58 |
| 73 | −38.1 | −34.8 | −31.5 | 190,100 | 468,500 | 960,800 | 2.46 |
| 86 | −38.8 | −35.6 | −32.7 | 192,000 | 430,100 | 704,500 | 2.24 |

TABLE 22

NMR Data for Linear Polymer

| Trans 1,4- BD | Cis 1,4- BD | 1,2- BD | DVCH | Styrene | Styrene Sequence | | | |
|---|---|---|---|---|---|---|---|---|
| | | | | | 1S | 2-4S | >/=5S | PyrES |
| 22.1 | 15.5 | 37.5 | 4.9 | 19.6 | 17.5 | 1.9 | 0.2 | 0.4 |

EXAMPLES 106–108

High Trans SBR

Polymerization of styrene, 1-pyrrolidino-ethyl styrene (PES) and butadiene was carried out in a one-gallon glass bowl batch reactor, under a blanket of nitrogen, equipped with a mechanical stirrer and temperature control via cooling water and low pressure steam. Both butadiene and styrene premixes contained approximately 20% monomer dissolved in hexane. The reactor was charged with 1% PES, 9% styrene in hexane and 90% butadiene in hexane to synthesize the appropriate polymer. The catalyst was added at room temperature, and within minutes of addition, the reactor temperature was 90° C. The catalyst system for this polymer consisted of an alkylated Barium diethyleneglycol ethylether (BaDEGEE) and Trioctyl aluminum (TOA) in a 1 (BaDEGEE) to 4 (TOA) ratio and n-butylithium. The addition of this catalyst is crictical for a successful polymerization. The alkylated BaDEGEE and TOA solution was prepared by added the appropriate amount of TOA to BaDEGEE and heated for 30 minutes at 70° C. Pyrrolidine and TMEDA can also be used as a modifier in this catalyst in a ratio of 1/1 amine/BaDEGEE, and they are typically added in this alkylation step. Here, 0.80 mmol of BaDEGEE per 100 grams of polymer was used to intiate polymerization. The alkylated BaDEGEE/TOA solution (with or without amine present) was added to a clean bottle and the correct amount of n-BuLi (in a ratio of 3 n-BuLi to 1 BaDEGEE) was added. The final solution had a ratio of 1/4/3/1 BaDEGEE/TOA/n-BuLi/amine (if used). This solution was shaken for several minutes at room temperature, and then it was injected as the initiator. Samples were taken over the course of the reaction to determine monomer conversion. According to gas chromatography, the PES monomer appeared to react much faster than the butadiene or styrene, see FIG. 1. All reactions were short-stopped with denatured ethanol, and 2,6-ditertbutylphenol was added to the polymer cement. The polymer was then dried for several days in a hot oven to make sure all solvent had evaporated. Table 1 summarizes the data for this system:

High Trans IBR

Using the same procedure and catalyst system as above, polymerization of PES, isoprene and butadiene was carried out. The only difference was that the reactor was charged with 1% PES, 9% isoprene and 90% butadiene. All other conditions were identical. FIG. 2 illustrates monomer conversion versus time. Polymer characteristics are shown in Table 1.

High Trans SIBR

Using the same procedure and catalyst system outlined above, polymerization of PES, styrene, isoprene and butadiene was carried out. The only difference was that the reactor was charged with 1% PES, 9% isoprene+styrene (2.5, 4.5 and 7.5% isoprene) and 90% butadiene. All other conditions were identical.

TABLE 23

Polymer characteristics for PES containing high trans polymers

| Sample | Tg (onset) | Tg (midpt.) | Tm | Mn | Mw | PDI | ML + 4 |
|---|---|---|---|---|---|---|---|
| 1/9/90 HTPESSBR | −83.4° C. | −76.0° C. | 24.2° C. | 135K | 191K | 1.42 | 57 |
| 10/90 HTSBR | −86.0° C. | −79.7° C. | 17.6° C. | 102K | 164K | 1.61 | 66 |

TABLE 24

NMR Results for PyrES High Trans polymers

| Sample | Trans 1,4-BD | Cis 1,4-BD | 1,2-BD | Styrene | PyrES |
|---|---|---|---|---|---|
| 1/9/90 HTPESSBR | 76.0 | 13.2 | 3.4 | 6.5 | 0.9 |
| 10/90 HTSBR | 75.2 | 13.8 | 3.5 | 7.5 | — |

What is claimed is:

1. A process for synthesizing an amine functionalized monomer that comprises (1) reacting a secondary amine with a 2,3-dihalopropene to produce a vinyl halide containing tertiary amine having the structural formula

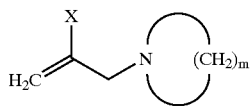

wherein m represents an integer from 4 to 10, and wherein X represents a halogen atom; and (2) reacting the vinyl halide containing tertiary amine with a vinyl magnesium halide to produce the monomer, wherein vinyl halide containing tertiary amine is reacted with the vinyl magnesium halide in a polar organic solvent, and wherein the monomer is of the structural formula

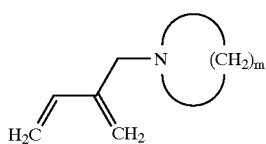

wherein m represents an integer from 4 to 10.

2. A process as specified in claim 1 wherein X represents chlorine or bromine.

3. A process as specified in claim 2 wherein m represents 4 or 6.

4. A process as specified in claim 1 wherein the 2,3-dihalopropene is 2,3-bromopropene.

5. A process as specified in claim 1 wherein the secondary amine is reacted with the 2,3-dihalopropene in the first step at a temperature which is within the range of −20° C. to 60° C.

6. A process as specified in claim 1 wherein the secondary amine is reacted with the 2,3-dihalopropene in the first step in the presence of an organic solvent.

7. A process as specified in claim 6 wherein the organic solvent is an ether.

8. A process as specified in claim 7 wherein the ether is diethyl ether.

9. A process as specified in claim 1 wherein the vinyl halide containing tertiary amine is reacted with the vinyl magnesium halide in the second step at a temperature which is within the range of −20° C. to 60° C.

10. A process as specified in claim 1 wherein the polar organic solvent is tetrahydrofuran.

11. A process as specified in claim 1 wherein the polar organic solvent is diethyl ether.

12. A process as specified in claim 1 wherein m represents the integer 4.

13. A process as specified in claim 1 wherein m represents the integer 6.

14. A process as specified in claim 13 wherein X represents bromine.

15. A process as specified in claim 14 wherein the secondary amine is reacted with the 2,3-dihalopropene in the first step at a temperature which is within the range of −20° C. to 60° C., and wherein the vinyl halide containing tertiary amine is reacted with the vinyl magnesium halide is the second step at a temperature which is within the range of −20° C. to 60° C.

16. A process as specified in claim 15 wherein the polar organic solvent is diethyl ether.

17. A process as specified in claim 16 wherein the secondary amine is reacted with the 2,3-dihalopropene in the first-step at a temperature which is within the range of 0° C. to 30° C., and wherein the vinyl halide containing tertiary amine is reacted with the vinyl magnesium halide in the second step at a temperature which is within the range of 0° C. to 30° C.

* * * * *